United States Patent
Kiso et al.

(10) Patent No.: US 9,657,129 B2
(45) Date of Patent: May 23, 2017

(54) CYCLIC AMINE COMPOUND AND PROCESS FOR PRODUCING POLYURETHANE RESIN BY USING IT

(75) Inventors: Hiroyuki Kiso, Shunan (JP); Takao Suzuki, Shunan (JP); Yoshihiro Takahashi, Shunan (JP)

(73) Assignee: TOSOH CORPORATION, Shunan (JP)

( * ) Notice: Subject to any disclaimer, the term of this patent is extended or adjusted under 35 U.S.C. 154(b) by 263 days.

(21) Appl. No.: 13/996,642

(22) PCT Filed: Dec. 22, 2011

(86) PCT No.: PCT/JP2011/079923
§ 371 (c)(1),
(2), (4) Date: Jun. 27, 2013

(87) PCT Pub. No.: WO2012/086807
PCT Pub. Date: Jun. 28, 2012

(65) Prior Publication Data
US 2013/0289232 A1 Oct. 31, 2013

(30) Foreign Application Priority Data

| Dec. 22, 2010 | (JP) | 2010-286693 |
| Dec. 24, 2010 | (JP) | 2010-288889 |
| Dec. 28, 2010 | (JP) | 2010-291795 |
| Oct. 18, 2011 | (JP) | 2011-229142 |
| Oct. 18, 2011 | (JP) | 2011-229143 |
| Nov. 2, 2011 | (JP) | 2011-241495 |
| Nov. 24, 2011 | (JP) | 2011-256401 |

(51) Int. Cl.
C08G 18/20 (2006.01)
C08G 18/38 (2006.01)
C08G 18/28 (2006.01)
C08G 18/32 (2006.01)
C07D 487/08 (2006.01)
C08G 18/76 (2006.01)
C08G 18/40 (2006.01)
C08G 18/48 (2006.01)
C08G 101/00 (2006.01)

(52) U.S. Cl.
CPC ....... *C08G 18/2063* (2013.01); *C07D 487/08* (2013.01); *C08G 18/2815* (2013.01); *C08G 18/2875* (2013.01); *C08G 18/3275* (2013.01); *C08G 18/3848* (2013.01); *C08G 18/4009* (2013.01); *C08G 18/4804* (2013.01); *C08G 18/7664* (2013.01); *C08G 2101/005* (2013.01); *C08G 2101/0008* (2013.01); *C08G 2101/0058* (2013.01); *C08G 2101/0083* (2013.01)

(58) Field of Classification Search
CPC .............. C07D 487/08; C08G 18/2063; C08G 18/2815; C08G 18/3848; C08G 18/2875; C08G 18/3275

See application file for complete search history.

(56) References Cited

U.S. PATENT DOCUMENTS

| 3,520,835 A | 7/1970 | Chandley et al. |
| 4,007,140 A | 2/1977 | Ibbotson |
| 4,026,840 A | 5/1977 | Bechara et al. |
| 4,248,930 A | 2/1981 | Haas et al. |
| 4,590,223 A | 5/1986 | Arai et al. |
| 5,086,178 A | 2/1992 | Banks |
| 5,143,944 A | 9/1992 | Savoca et al. |
| 5,710,191 A | 1/1998 | Listemann et al. |
| 6,232,356 B1 * | 5/2001 | Mercando et al. ........... 521/129 |
| 2008/0015273 A1 | 1/2008 | Burdeniuc et al. |
| 2011/0077376 A1* | 3/2011 | Tokumoto et al. ............. 528/68 |

FOREIGN PATENT DOCUMENTS

| CA | 2 609 308 | 11/2006 |
| CA | 2 726 202 | 12/2009 |
| GB | 1 338 275 | 11/1973 |
| JP | S42-016312 | 9/1967 |
| JP | 45-003114 | 2/1970 |

(Continued)

OTHER PUBLICATIONS

International Search Report for PCT/JP2011/079923, mailed Feb. 7, 2012.

(Continued)

*Primary Examiner* — Rabon Sergent
(74) *Attorney, Agent, or Firm* — Nixon & Vanderhye P.C.

(57) ABSTRACT

To provide a novel cyclic amine compound and a process for producing a polyurethane resin by using it. A 3-hydroxy-1,5-diazabicyclo[3.2.2]nonane represented by the following formula (1), and a process for producing a polyurethane resin by using a catalyst for producing a polyurethane resin, which contains the 3-hydroxy-1,5-diazabicyclo[3.2.2] nonane. When the compound represented by the formula (1) has optical isomers, diastereomers or geometric isomers, the compound includes both a mixture of any of them and an isolated isomer of any of them.

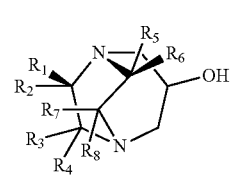

(1)

[in the above formula (1), each of $R_1$, $R_2$, $R_3$, $R_4$, $R_5$, $R_6$, $R_7$ and $R_8$ which are independent of one another, is a hydrogen atom, a $C_{1-4}$ alkyl group, a hydroxy group, a hydroxymethyl group or a $C_{1-4}$ alkoxy group.]

15 Claims, 4 Drawing Sheets

(56) References Cited

FOREIGN PATENT DOCUMENTS

| | | |
|---|---|---|
| JP | B-45-3114 | 2/1970 |
| JP | A-46-4846 | 11/1971 |
| JP | B-61-31727 | 7/1986 |
| JP | A-63-265909 | 11/1988 |
| JP | 10-324728 | 12/1998 |
| JP | 2971979 | 8/1999 |
| JP | A-2008-45113 | 2/2008 |
| JP | A-2010-37488 | 2/2010 |
| JP | A-2010-106192 | 5/2010 |
| WO | WO 2009/145320 | 12/2009 |

OTHER PUBLICATIONS

Keiji Iwata, "Polyurethane Resin Handbook", (First Edition in 1987), Nikkan Kogyo Shimbun, Ltd., p. 118.
J. Am. Chem. Soc., 76, 1126 (1954).
International Preliminary Report on Patentability in PCT/JP2011/079923 dated Jul. 11, 2013.
Listemann, M.L. et al., "The Influence of Tertiary Amine Structure on Blow-to-Gel Selectivity",Polyurethanes World Congress 1993, Oct. 10-13, pp. 595-608.
otice of Opposition in Ep App. No. 11850399.4, mailed Feb. 10, 2016.

\* cited by examiner

CYCLIC AMINE COMPOUND AND PROCESS FOR PRODUCING POLYURETHANE RESIN BY USING IT

This application is the U.S. national phase of International Application No. PCT/JP2011/079923 filed 22 Dec. 2011 which designated the U.S. and claims priority to JP Patent Application Nos. 2010-286693 filed 22 Dec. 2010, 2010-288889 filed 24 Dec. 2010, 2010-291795 filed 28 Dec. 2010, 2011-229142 filed 18 Oct. 2011, 2011-229143 filed 18 Oct. 2011, 2011-241495 filed Nov. 2, 2011 and 2011-256401 filed 24 Nov. 2011, the entire contents of each of which are hereby incorporated by reference.

TECHNICAL FIELD

The present invention relates to a novel cyclic amine compound containing a hydroxy group, a catalyst for producing a polyurethane resin, containing it, and a process for producing a polyurethane resin by using it.

BACKGROUND ART

Amine compounds have heretofore been used for various applications, for example, as intermediates for the production of various drugs or pigments, as charge transport materials for organic electroluminescent elements, as curing agents for epoxy resins, and as functional materials including catalysts for the production of polyurethanes. Among them, 1,4-diazabicyclo[2.2.2]octane (hereinafter referred to simply as "TEDA") being a cyclic amine compound, has a strong nucleophilicity and is widely used as a basic catalyst for various organic reactions, particularly as a general-purpose gelling catalyst in the field of polyurethane resins.

A polyurethane resin is usually produced by reacting a polyol and a polyisocyanate in the presence of a catalyst and, as the case requires, a blowing agent, a surfactant, a flame retardant, a cross-linker, etc. For the production of polyurethane resins, many metal-type compounds or tertiary amine compounds are used as catalysts. They are used alone or in combination industrially frequently.

In the production of polyurethane foams wherein water, a low boiling point organic compound or both of them are used as a blowing agent, among such catalysts, tertiary amine compounds are particularly widely used, since the productivity and formability are thereby excellent. Such tertiary amine compounds include, in addition to the above-mentioned TEDA, e.g. N,N,N',N'-tetramethyl-1,6-hexanediamine, bis(2-dimethylaminoethyl)ether, N,N,N',N'',N''-pentamethyldiethylenetriamine, N-methylmorpholine, N-ethylmorpholine, N,N-dimethylethanolamine, etc. (e.g. Non-patent Document 1). As the metal-type catalysts, organic metal compounds such as organic tin compounds are, for example, frequently used, but as the productivity or formability is thereby deteriorated, they are rarely used alone, and in most cases, they are used in combination with a tertiary amine catalyst.

Among them, the tertiary amine compounds are gradually leaked as volatile amines from polyurethane products and are likely to cause, e.g. in the case of interior parts for automobiles, etc., an odor problem or a discoloration problem of other materials (e.g. PVC leather) by the volatile amines. Further, the tertiary amine catalysts usually have a strong odor, whereby the working environment is seriously deteriorated under the production of polyurethane resins. As a method to solve such problems, it has been proposed to use, instead of such volatile tertiary amine catalysts, amine catalysts (so-called "reactive catalysts") having a hydroxy group or a primary or secondary amino group reactive with a polyisocyanate in their molecules, or bifunctional cross-linkers having a tertiary amino group in their molecules (e.g. Patent Documents 1 to 6).

According to the above Patent Documents, such amine compounds are fixed in the polyurethane bond network by reacted with polyisocyanates, whereby the above problems can be avoided. Such a method can be regarded as a method effective to reduce the odor of the final resin products. However, such amine catalysts are poor in the activity for the gelling reaction (the reaction of a polyol and an isocyanate), and thus, there is a problem such that the curing properties of polyurethane resins tend to be low. Whereas, the method of using the above cross-linkers is effective to reduce the odor of the final polyurethane resin products and to improve the working environment at the time of the production of the polyurethane resins, but the physical properties such as the hardness of the polyurethane resins tend to be thereby inadequate.

On the other hand, the metal-type compounds do not cause the odor problem or the problem to deteriorate other materials like the above-mentioned tertiary amine catalysts. However, if a metal-type compound is used alone, the productivity, physical properties, moldability, etc., tend to deteriorate, and among metal-type catalysts, there are ones containing a heavy metal such as lead, tin, mercury or the like, which are likely to cause a toxicity problem or an environmental problem due to the heavy metal remaining in the products.

Under the circumstances, the applicants have already filed patent applications (e.g. Patent Documents 7 and 8) relating to a process for producing a polyurethane resin by using 2-hydroxymethyltriethylenediamine as a catalyst. However, it is necessary to suitably select a catalyst to be used, depending upon the particular purpose of a polyurethane resin product, and it is further desired to develop a process for producing a polyurethane resin without using a catalyst containing a heavy metal.

Further, 1,5-diazabicyclo[3.2.2]nonane being a cyclic amine compound has been proposed as a catalyst for producing a polyurethane resin (e.g. Patent Document 9), and its physical properties are reported in Non-patent Document 2. However, there has been no report with respect to a 3-hydroxy-1,5-diazabicyclo[3.2.2]nonane having a hydroxy group introduced to a specific position of 1,5-diazabicyclo [3.2.2]nonane.

PRIOR ART DOCUMENTS

Patent Documents

Patent Document 1: JP-A-46-4846
Patent Document 2: JP-B-61-31727
Patent Document 3: Japanese Patent No. 2,971,979
Patent Document 4: JP-A-63-265909
Patent Document 5: JP-A-2008-45113
Patent Document 6: U.S. Pat. No. 4,007,140
Patent Document 7: JP-A-2010-37488
Patent Document 8: JP-A-2010-106192
Patent Document 9: JP-B-45-3114

Non-Patent Documents

Non-patent Document 1: Keiji Iwata, "Polyurethane Resin Handbook", (First edition in 1987), Nikkan Kogyo Shimbun, Ltd., p. 118

Non-patent Document 2: J. Am. Chem. Soc., 76, 1126 (1954)

DISCLOSURE OF INVENTION

Technical Problem

The present invention has been made in view of the above-mentioned background of prior art, and its purpose is to provide a 3-hydroxy-1,5-diazabicyclo[3.2.2]nonane, as a novel cyclic amine compound having a hydroxy group at a specific position.

Another object of the present invention is to provide a process for producing a polyurethane resin, whereby by using a catalyst containing the cyclic amine compound, it is possible to obtain a polyurethane product with good productivity and formability without bringing about the odor problem or the toxicity or environmental problem.

Solution to Problem

The present inventors have conducted extensive studies to solve the above problems and as a result, they have found the 3-hydroxy-1,5-diazabicyclo[3.2.2]nonane and accomplished the present invention.

That is, as described below, the present invention relates to a novel cyclic amine compound containing a hydroxy group, a catalyst for producing a polyurethane resin, containing it, and a process for producing a polyurethane resin by using it.

[1] A 3-hydroxy-1,5-diazabicyclo[3.2.2]nonane represented by the following formula (1), provided that when the compound represented by the formula (1) has optical isomers, diastereomers or geometric isomers, the compound includes both a mixture of any of them and an isolated isomer of any of them:

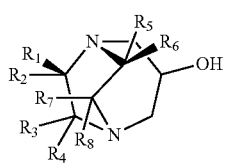

(1)

[in the above formula (1), each of $R_1$, $R_2$, $R_3$, $R_4$, $R_5$, $R_6$, $R_7$ and $R_8$ which are independent of one another, is a hydrogen atom, a $C_{1-4}$ alkyl group, a hydroxy group, a hydroxymethyl group or a $C_{1-4}$ alkoxy group.]

[2] The 3-hydroxy-1,5-diazabicyclo[3.2.2]nonane according to the above [1], wherein in the formula (1), among $R_1$, $R_2$, $R_3$, $R_4$, $R_5$, $R_6$, $R_7$ and $R_8$, at least one is a methyl group or a hydroxymethyl group.

[3] The 3-hydroxy-1,5-diazabicyclo[3.2.2]nonane according to the above [1], wherein in the formula (1), $R_1$, $R_2$, $R_3$, $R_4$, $R_5$, $R_6$, $R_7$ and $R_8$ are all hydrogen atoms.

[4] A catalyst for producing a polyurethane resin, which contains the 3-hydroxy-1,5-diazabicyclo[3.2.2]nonane as defined in any one of the above [1] to [3].

[5] A catalyst for producing a polyurethane resin, which contains the above 3-hydroxy-1,5-diazabicyclo[3.2.2]nonane and a hydroxyalkyl-substituted-1,4-diazabicyclo[2.2.2]octane (B) represented by the following formula (2), provided that when the compound represented by the formula (2) has optical isomers, diastereomers or geometric isomers, the compound includes both a mixture of any of them and an isolated isomer of any of them:

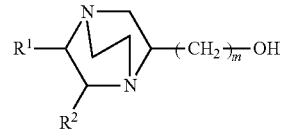

(2)

[in the above formula (2), each of $R^1$ and $R^2$ which are independent of each other, is a hydrogen atom, a $C_{1-4}$ alkyl group, a hydroxy group, a hydroxymethyl group or a $C_{1-4}$ alkoxy group, and m is 1 or 2.]

[6] The catalyst for producing a polyurethane resin according to the above [5], wherein in the formula (2), each of $R^1$ and $R^2$ which are independent of each other, is a hydrogen atom, a methyl group, an ethyl group or a hydroxymethyl group (provided that $R^1$ and $R^2$ are not all the same substituents).

[7] The catalyst for producing a polyurethane resin according to the above [5] or [6], wherein in the formula (2), $R^1$ and $R^2$ are all hydrogen atoms.

[8] The catalyst for producing a polyurethane resin according to any one of the above [5] to [7], which contains the 3-hydroxy-1,5-diazabicyclo[3.2.2]nonane (A) in an amount of from 1 to 30 wt % to the hydroxyalkyl-substituted-1,4-diazabicyclo[2.2.2]octane (B).

[9] A catalyst for producing a polyurethane resin, which contains the above 3-hydroxy-1,5-diazabicyclo[3.2.2]nonane (A), the above hydroxyalkyl-substituted-1,4-diazabicyclo[2.2.2]octane (B) and an aminourea derivative (C).

[10] The catalyst for producing a polyurethane resin according to the above [9], wherein the hydroxyalkyl-substituted-1,4-diazabicyclo[2.2.2]octane (B) is an amine compound represented by the following formula (2a):

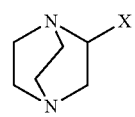

(2a)

[in the formula (2a), X is a hydroxy group, a hydroxymethyl group or a hydroxyethyl group.]

[11] The catalyst for producing a polyurethane resin according to the above [9] or [10], wherein the aminourea derivative (C) is at least one member selected from the group consisting of a mono(tertiary aminoalkyl)urea, a bis(tertiary aminoalkyl)urea and a mixture thereof.

[12] The catalyst for producing a polyurethane resin according to any one of the above [9] to [11], wherein the aminourea derivative (C) is one or more compounds selected from the group consisting of 2-dimethylaminoethylurea, N,N'-bis(2-dimethylaminoethyl)urea, N,N-bis(2-dimethylaminoethyl)urea, 3-dimethylaminopropylurea, N,N'-bis(3-dimethylaminopropyl)urea, N,N-bis(3-dimethylaminopropyl)urea, 1-(N-methyl-3-pyrrolidino)methylurea, 1,3-bis(N-methyl-3-pyrrolidino)methylurea, 3-piperidinopropylurea, N,N'-bis(3-piperidinopropyl)urea, 3-morpholinopropylurea, N,N'-bis(3-morpholinopropyl)urea, 2-piperidinoethylurea, N,N'-bis(2-piperidinoethyl)urea, 2-morpholinoethylurea and N,N'-bis(2-morpholinoethyl)urea.

[13] The catalyst for producing a polyurethane resin according to any one of the above [4] to [12], which does not contain lead, tin, mercury or any compound thereof.
[14] A process for producing a polyurethane resin, which comprises reacting a polyol and a polyisocyanate in the presence of the catalyst for producing a polyurethane resin as defined in any one of the above [4] to [13].
[15] The process for producing a polyurethane resin according to the above [14], wherein the amount of the catalyst for producing a polyurethane resin as defined in any one of the above [4] to [13] to be used, is within a range of from 0.01 to 30 parts by weight per 100 parts by weight of the polyol.

Advantageous Effects of Invention (1) The 3-hydroxy-1,5-diazabicyclo[3.2.2]nonane represented by the above formula (1) as a novel cyclic amine compound of the present invention, has a high catalytic activity and is little leaked as a volatile amine, and it is thus suitably useful for the production of a polyurethane resin.
(2) The catalyst for producing a polyurethane resin, which contains the 3-hydroxy-1,5-diazabicyclo[3.2.2]nonane represented by the above formula (1) and the hydroxyalkyl-substituted-1,4-diazabicyclo[2.2.2]octane represented by the above formula (2), has a high catalytic activity and is very little leaked as a volatile amine, and it is thus suitably useful for the production of a polyurethane resin.
(3) In the polyurethane resin produced by using the catalyst for producing a polyurethane resin, which contains the 3-hydroxy-1,5-diazabicyclo[3.2.2]nonane represented by the above formula (1), the hydroxyalkyl-substituted-1,4-diazabicyclo[2.2.2]octane represented by the above formula (2), and the aminourea derivative, an amine that volatilizes from the polyurethane resin is very little, and it is possible to further improve the catalytic activity while preventing the odor of the amine catalyst from the obtained foam and maintaining the formability of the foam.
(4) Further, the catalyst for producing a polyurethane resin of the present invention has a high catalytic activity, and it is thereby possible to produce a polyurethane product with good productivity and formability without using at least one metal-type catalyst selected from the group consisting of lead, tin, mercury and their compounds for the production of the polyurethane resin, and further, without causing the odor problem or the toxicity or environmental problem, it is effective to prevent discoloration of PVC (polyvinyl chloride) in an automobile instrument panel as caused by a usual amine catalyst or to prevent fogging of window glass due to a volatile component that volatilizes from the foam.

DESCRIPTION OF EMBODIMENTS

Figure 1:
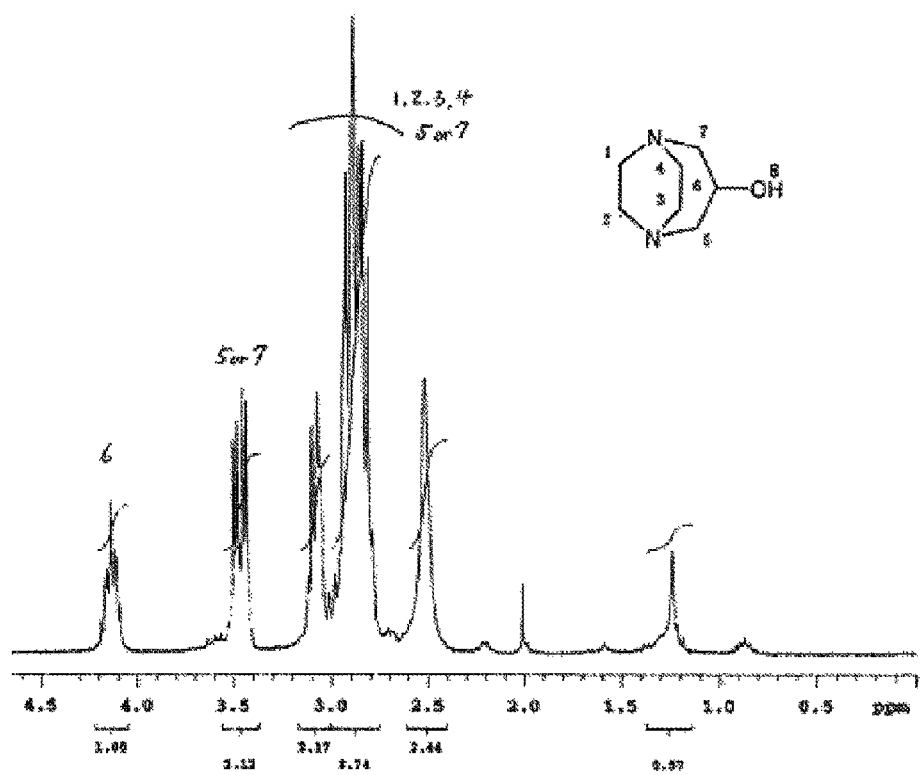
FIG. 1 shows the $^1$H-NMR spectrum of a compound identified by exemplified compound No. 1-1.

Firstly, the 3-hydroxy-1,5-diazabicyclo[3.2.2]nonane of the present invention will be described.
The 3-hydroxy-1,5-diazabicyclo[3.2.2]nonane of the present invention is an amine compound represented by the above formula (1).
In the present invention, when the compound represented by the above formula (1) has optical isomers, diastereomers and geometric isomers, the compound represented by the above formula (1) includes both a mixture of any of them and an isolated isomer of any of them.
In the above formula (1), substituents $R_1$, $R_2$, $R_3$, $R_4$, $R_5$, $R_6$, $R_7$ and $R_8$ are not particularly limited so long as they correspond to the above definitions, and each of them may, for example, be a hydrogen atom, a hydroxy group, a hydroxymethyl group, a $C_{1-4}$ alkyl group (such as a methyl group, an ethyl group, a n-propyl group, an isopropyl group, a n-butyl group, an isobutyl group, a sec-butyl group or a tert-butyl group) or a $C_{1-4}$ alkoxy group (such as a methoxy group, an ethoxy group, a n-propoxy group, an isopropoxy group, a n-butoxy group or a sec-butoxy group). Preferred is a hydrogen atom, a methyl group, an ethyl group, a hydroxymethyl group or a methoxy group.
A preferred compound in the present invention may, for example, be a compound of the above formula (1) wherein among $R_1$, $R_2$, $R_3$, $R_4$, $R_5$, $R_6$, $R_7$ and $R_8$, at least one is a methyl group or a hydroxy group or a compound of the formula (1) wherein $R_1$, $R_2$, $R_3$, $R_4$, $R_5$, $R_6$, $R_7$ and $R_8$ are all hydrogen atoms i.e. 3-hydroxy-1,5-diazabicyclo[3.2.2] nonane. 3-Hydroxy-1,5-diazabicyclo[3.2.2]nonane is preferred also from the viewpoint of the catalytic activity for the production of a polyurethane resin.
Specific examples of the amine compound represented by the above formula (1) include e.g. the following compounds, but the present invention is by no means limited thereto.
Exemplified Compound Nos.

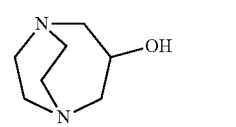

1-1

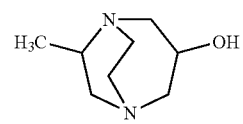

1-2

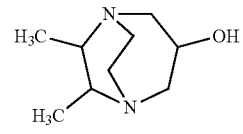

1-3

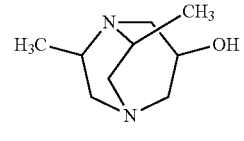

1-4

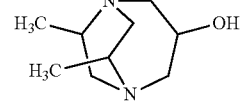

1-5

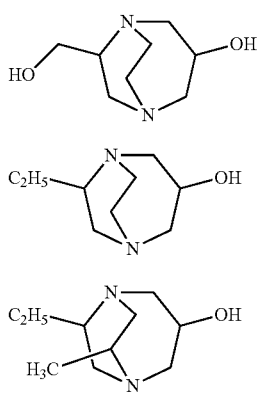

The process for producing the amine compound represented by the formula (1) is not particularly limited, but it may, for example, be produced by a cyclization reaction of 3-(1'-piperazinyl)-1,2-propanediol. This reaction may be carried out in a gas phase or in a liquid phase. Further, this reaction may be carried out by a slurry-bed batch, semi-batch or continuous system, or a fixed-bed flow system, but industrially, a fixed-bed flow system is advantageous from the viewpoint of the operation, apparatus and economical efficiency.

Among the amine compounds represented by the formula (1), one having a substituent may be produced, for example, by using the corresponding substituted piperazine as the starting material. The process for producing the substituted piperazine is not particularly limited, and it may be produced by a known method, for example, by an intramolecular ring-closing reaction of a propylene oxide-adduct of ethylenediamine, or by a method disclosed in J. Med. Chem., 36, 2075 (1999). Specifically, 2-methylpiperazine is a compound which is available as a commercial product or by a known method, for example, by an intermolecular ring-closing reaction of a propylene oxide-adduct of ethylenediamine. Whereas, 2-hydroxymethylpiperazine is a compound which is available by a known method, for example, by a method disclosed in J. Med. Chem., 36, 2075 (1999).

The amine compound represented by the above formula (1) is suitably used as a catalyst for the production of a polyurethane resin.

Now, the catalyst for producing a polyurethane resin of the present invention will be described.

The catalyst for producing a polyurethane resin of the present invention is characterized in:

(1) that it contains a 3-hydroxy-1,5-diazabicyclo[3.2.2]nonane (A) represented by the above formula (1), (2) that it contains a 3-hydroxy-1,5-diazabicyclo[3.2.2]nonane (A) represented by the above formula (1) and a hydroxyalkyl-substituted-1,4-diazabicyclo[2.2.2]octane (B) represented by the above formula (2), or (3) that it contains a 3-hydroxy-1,5-diazabicyclo[3.2.2]nonane (A) represented by the above formula (1), a hydroxyalkyl-substituted-1,4-diazabicyclo[2.2.2]octane (B) represented by the above formula (2), and an aminourea derivative (C).

Hereinafter, the 3-hydroxy-1,5-diazabicyclo[3.2.2]nonane (A) represented by the above formula (1) may sometimes be referred to as "the amine compound (A) represented by the above formula (1)", and the hydroxyalkyl-substituted-1,4-diazabicyclo[2.2.2]octane (B) represented by the above formula (2) may sometimes be referred to as "the amine compound (B) represented by the above formula (2)".

The catalyst for producing a polyurethane resin of the present invention is capable of sufficiently accomplishing the objects of the present invention by using the 3-hydroxy-1,5-diazabicyclo[3.2.2]nonane (A) represented by the above formula (1) and therefore, is not required to use other catalysts in combination. However, as the above-mentioned further effects can be obtained, a hydroxyalkyl-substituted-1,4-diazabicyclo[2.2.2]octane (B) represented by the above formula (2), and an aminourea derivative (C), may further be used in combination.

The amine compound (A) represented by the above formula (1) can suitably be used as a gelling catalyst to activate the reaction of a polyol and a isocyanate compound. Further, the amine compound (A) represented by the above formula (1) can be regarded as a reactive gelling catalyst, since it is reactive with an isocyanate group derived from a polyisocyanate in the production process for a polyurethane resin.

In the present invention, when the compound corresponding to the above formula (2) has optical isomers, diastereomers and geometrical isomers, the amine compound (B) represented by the above formula (2) includes both a mixture of any of them and an isolated isomer of any of them.

In the above formula (2), substituents $R^1$ and $R^2$ are not particularly limited so long as they correspond to the above definitions, and each of them may, for example, be a hydrogen atom, a hydroxy group, a hydroxymethyl group, a $C_{1-4}$ alkyl group (such as a methyl group, an ethyl group, a n-propyl group, an isopropyl group, a n-butyl group, an isobutyl group, a sec-butyl group or a tert-butyl group) or a $C_{1-4}$ alkoxy group (such as a methoxy group, an ethoxy group, a n-propoxy group, an isopropoxy group, a n-butoxy group or a sec-butoxy group). Among them, preferred is a hydrogen atom, a methyl group, an ethyl group, a hydroxymethyl group or a methoxy group.

A preferred compound in the present invention may, for example, be a compound of the above formula (2) wherein each of substituents $R^1$ and $R^2$ which are independent of each other, is a hydrogen atom, a methyl group, an ethyl group or a hydroxymethyl group (provided that $R^1$ and $R^2$ are not all the same substituents), or a compound of the above formula (2) wherein substituents $R^1$ and $R^2$ are all hydrogen atoms. The compound of the above formula (2) wherein substituents $R^1$ and $R^2$ are all hydrogen atoms, exhibits a preferred performance also in the catalytic activity in the production of a polyurethane resin.

As the amine compound (B) represented by the above formula (2), an amine compound represented by the following formula (2a) may, for example, be exemplified as a preferred one:

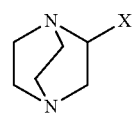

(2a)

[wherein X is a hydroxy group, a hydroxymethyl group or a hydroxyethyl group.]

Specific examples for the amine compound (B) represented by the above formula (2) include e.g. the following compounds, but the present invention is by no means limited thereto.

Exemplified Compound Nos.

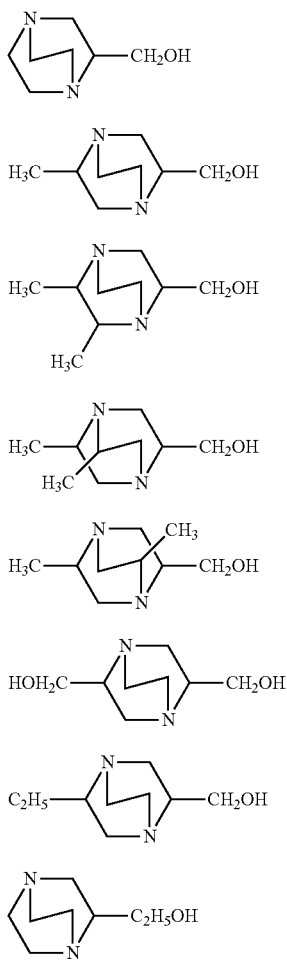

The process for producing the amine compound (B) represented by the formula (2) is not particularly limited, but it may be produced, for example, by a method disclosed in Khimiya Geterotsiklicheskikh Soedinenil, 10, 1404 (1980) or in WO95/18104.

Further, it may be produced also by intramolecular cyclization of an ethylene oxide adduct of a hydroxyalkylpiperazine to be induced by e.g. a method disclosed in Journal of Medical Chemistry (1993), 36 (15), 2075-2083 or in JP-A-2010-120887.

Still further, it may be produced also by a method disclosed in JP-A-2010-37325, i.e. by a cyclization reaction of a dihydroxyalkylpiperazine. Among these methods, the production method by a cyclization reaction of a dihydroxyalkylpiperazine is preferred from the viewpoint of the reaction process and the production efficiency.

This cyclization reaction of a dihydroxyalkylpiperazine may be carried out in a gas phase or in a liquid phase, but, a gas phase reaction is preferred, since the reaction temperature is high. Further, this reaction may be carried out by a slurry-bed batch, semi-batch or continuous system, or a fixed-bed flow system, but industrially, a fixed-bed flow system is advantageous from the viewpoint of the operation, apparatus and economical efficiency.

The cyclization reaction of the dihydroxyalkylpiperazine is usually carried out in the presence of a catalyst. The catalyst to be used is not particularly limited, and it can be prepared, for example, by impregnating an inorganic salt to an inorganic carrier such silica, alumina, zeolite, zeorum, titania, zirconia or aluminum phosphate. The inorganic salt is not particularly limited, and, for example, a salt containing an alkali metal or an alkaline earth metal, or an inorganic phosphorus compound, may preferably be used.

With respect to the process for producing the amine compound (B) represented by the formula (2) having a substituent, such production is possible by using the corresponding substituted piperazine. The process for producing the substituted piperazine may be carried out in accordance with e.g. the above-mentioned known technique relating to synthesis of a hydroxyalkylpiperazine.

The process for producing the amine compound (A) represented by the formula (1) is, for example, as described above, but by further applying the above-mentioned process for producing the amine compound (B) represented by the formula (2) (i.e. the cyclization reaction of a dihydroxyalkylpiperazine), the amine compound may also be produced together with the amine compound represented by the formula (2).

The amine compound (B) represented by the formula (2) has a primary hydroxy group and thus has a high reactivity with an isocyanate group, whereby it is possible to substantially reduce a volatile amine in the polyurethane resin. However, when viewed as a catalyst, it has a large steric hindrance attributable to the substituent, in the vicinity of the nitrogen atom at one side of the TEDA structure. Accordingly, an unshared electron pair of the nitrogen atom activates the reaction of a polyol with an isocyanate via a hydrogen bond, and as the steric hindrance is large, the initial reactivity tends to be slow, and the amount of the catalyst to be required, tends to increase.

Whereas, the amine compound (A) represented by the above formula (1) has a small steric hindrance attributable to a hydroxy group in the vicinity of the nitrogen atom, whereby the catalytic activity is high as compared with the amine compound (B) represented by the above formula (2).

On the other hand, the amine compound (A) represented by the above formula (1) has a secondary hydroxy group, whereby the reactivity with an isocyanate group becomes low. Therefore, if the amine compound (A) represented by the above formula (1) is added excessively, it is likely to remain as an unreacted amine in the polyurethane product.

Therefore, with a view to satisfying both the improvement in the catalytic activity and the reduction of a volatile amine in the urethane foam, in a case where the amine compound (A) represented by the above formula (1) and the amine compound (B) represented by the above formula (2) are used in combination, it is preferred to use the amine compound (A) represented by the above formula (1) in an amount within a range of from 1 to 30 wt %, more preferably from 5 to 20 wt %, to the amine compound (B) represented by the above formula (2) (100 wt %).

In the present invention, the aminourea derivative (C) is not particularly limited, and may, for example, be at least one member selected from the group consisting of a mono (tertiary aminoalkyl)urea, a bis(tertiary aminoalkyl)urea and a mixture thereof.

Specifically, 2-dimethylaminoethyl urea, N,N'-bis(2-dimethylaminoethyl)urea, N,N-bis(dimethylaminoethyl)urea, 3-dimethylaminopropylurea, N,N'-bis(3-dimethylaminopropyl)urea, N,N-bis(3-dimethylaminopropyl)urea, 1-(N-methyl-pyrrolidino)methylurea, 1,3-bis(N-methyl-3-pyrrolidino)methylurea, 3-piperidinopropylurea, N,N'-bis(3-piperidinopropyl)urea, 3-morpholinopropylurea, N,N'-bis (3-morpholinopropyl)urea, 2-piperidinoethylurea, N,N'-bis (2-piperidinoethyl)urea, 2-morpholinoethylurea, N,N'-bis(2-morpholinoethyl)urea, etc., may be exemplified. Among them, 3-dimethylaminopropylurea or N,N'-bis(3-dimethylaminopropyl)urea is preferred as the aminourea derivative, since it is industrially available.

The aminourea derivative (C) may be produced by a known method. For example, it may be produced by reacting urea and the corresponding tertiary alkylamine in a suitable molar ratio while removing ammonia.

Now, the process for producing a polyurethane resin by using the above-described catalyst for producing a polyurethane resin of the present invention, will be described.

In the process of the present invention, the polyurethane resin is obtainable by reacting (curing) and foaming a polyol and a polyisocyanate in the presence of the catalyst for producing a polyurethane resin of the present invention and, as the case requires, additives such as additional catalysts, a blowing agent, a surfactant, a flame retardant, a cross-linker, etc. In the present invention, the catalyst is one to accelerate each of e.g. a urethane-forming reaction (gelling reaction) of a polyol and a polyisocyanate, an urea-forming reaction (blowing reaction) of a polyisocyanate and water, etc.

The polyol to be used in the present invention is not particularly limited and may, for example, be a conventional polyether polyol, polyester polyol or polymer polyol, or further a flame retardant polyol such as a phosphorus-containing polyol or halogen-containing polyol. These polyols may be used alone or may be used in combination as suitably mixed.

The polyether polyol is not particularly limited and may, for example, be one produced by using as a starting material a compound having at least two active hydrogen groups (specifically e.g. a polyhydric alcohol such as ethylene glycol, propylene glycol, glycerin, trimethylolpropane or pentaerythritol, an amine such as ethylenediamine, or an alkanolamine such as ethanolamine or diethanolamine, is exemplified) and subjecting it and an alkylene oxide (specifically e.g. ethylene oxide or propylene oxide is exemplified) to an addition reaction [e.g. a method disclosed in Gunter Oertel, "Polyurethane Handbook" (1985) Hanser Publication (Germany), p. 42-53].

The polyester polyol is not particularly limited and may, for example, be one obtainable by a reaction of a dibasic acid and glycol, or a polyester polyol obtained by treating a refuse from the production of nylon, a refuse of trimethylolpropane or pentaerythritol, a refuse of a phthalic acid-type polyester or a waste material [e.g. as disclosed in Keiji Iwata "Polyurethane Resin Handbook" (1987), Nikkan Kogyo Shimbun Ltd., p. 117].

The polymer polyol is not particularly limited and may, for example, be a polymer polyol obtained by reacting the above-mentioned polyether polyol and an ethylenically unsaturated monomer (e.g. butadiene, acrylonitrile, styrene or the like may be mentioned) in the presence of a radical polymerization catalyst.

The flame retardant polyol is not particularly limited and may, for example, be a phosphorus-containing polyol obtainable by adding an alkylene oxide to a phosphoric acid compound, a halogen-containing polyol obtainable by ring-opening polymerization of epichlorohydrin or trichlorobutylene oxide, or a phenol polyol.

In the present invention, a polyol having an average hydroxy value within a range of from 20 to 1,000 mgKOH/g is usually used. However, for a flexible polyurethane foam or a semi-rigid polyurethane foam, one having an average hydroxy value within a range of from 20 to 100 mgKOH/g is preferably used, and for a rigid polyurethane foam, one having an average hydroxy value within a range of from 100 to 800 mgKOH/g is preferably used.

The polyisocyanate to be used in the process of the present invention may be a conventional one and is not particularly limited. For example, an aromatic polyisocyanate such as toluene diisocyanate (hereinafter referred to also as "TDI"), diphenylmethane diisocyanate (hereinafter referred to also as "MDI"), naphthylene diisocyanate or xylylene diisocyanate, an aliphatic polyisocyanate such as hexamethylene diisocyanate, an alicyclic polyisocyanate such as dicyclohexyl diisocyanate or isophorone diisocyanate, or a mixture thereof, may, for example, be mentioned. Among them, preferred is TDI or its derivative, or MDI or its derivative. They may be used alone or in combination as mixed.

TDI or its derivative may, for example, be a mixture of 2,4-TDI and 2,6-TDI, or a terminal isocyanate prepolymer derivative of TDI.

MDI or its derivative may, for example, be a mixture of MDI and a polyphenylpolymethylene diisocyanate of its polymer, or a diphenylmethane diisocyanate having a terminal isocyanate group.

Among these isocyanates, TDI or its derivative, MDI or its derivative, or both of them, may suitably be used for a flexible polyurethane resin or semi-rigid polyurethane resin product. Whereas, for a rigid polyurethane resin, a mixture of MDI and a polyphenylpolymethylene diisocyanate of its polymer may be suitably used.

The blend ratio of the polyisocyanate to the polyol is not particularly limited, but it is usually preferably within a range of from 60 to 400, more preferably within a range of from 50 to 200, further preferably within a range of from 60 to 120, as represented by the isocyanate index ([isocyanate group]/[active hydrogen group reactive with isocyanate group]×100).

In the process of the present invention, as the catalyst, the catalyst for producing a polyurethane resin of the present invention may be used alone, and it is not required to use other catalysts. However, conventional other catalysts may also be used within a range not to depart from the concept of the present invention. As such other catalysts, a blowing catalyst, an organic metal catalyst, a metal carboxylate catalyst, a tertiary amine catalyst, a quaternary ammonium salt catalyst, etc. may be mentioned. However, in consideration of the toxicity and environmental problem, it is advisable not to use a metal-type catalyst selected from the group consisting of lead, tin, mercury and their compounds.

The blowing catalyst may be a conventional one and is not particularly limited. For example, triethanolamine, bisdimethylaminoethyl ether, N,N,N',N'',N''-pentamethyldiethylenetriamine, hexamethyltriethylenetetramine, N,N-dimethylaminoethoxyethanol, N,N,N'-trimethylaminoethylethanolamine, N,N-dimethylaminoethyl-N'-methylaminoethyl-N''-methylaminoisopropanol or N,N,N'-trimethyl-N'-(2-hydroxyethyl)-bis(2-aminoethyl)ether may be mentioned.

The organic metal catalyst may be a conventional one and is not particularly limited. For example, stannous diacetate, stannous dioctoate, stannous dioleate, stannous dilaurate, dibutyltin oxide, dibutyltin diacetate, dibutyltin dilaurate, dibutyltin dichloride, dioctyltin dilaurate, lead octanoate, lead naphthenate, nickel naphthenate or cobalt naphthenate, may be mentioned.

The metal carboxylate catalyst may be a conventional one and is not particularly limited. For example, an alkali metal salt or alkaline earth metal salt of a carboxylic acid may be mentioned. Here, the carboxylic acid is not particularly limited and may, for example, be an aliphatic mono- or di-carboxylic acid such as acetic acid, propionic acid, 2-ethylhexanoic acid or adipic acid, or an aromatic mono- or di-carboxylic acid such as benzoic acid or phthalic acid. Further, as the metal to form a carboxylate, an alkali metal such as lithium, sodium or potassium, or an alkaline earth metal such as calcium or magnesium, may, for example, be mentioned as preferred.

The tertiary amine catalyst may be a conventional one and is not particularly limited. For example, tertiary amine compounds such as N,N,N',N'-tetramethylethylenediamine, N,N,N',N'-tetramethylpropylenediamine, N,N,N',N'',N''-pentamethyldiethylenetriamine, N,N,N',N'',N''-pentamethyl-(3-aminopropyl)ethylenediamine, N,N,N',N'',N''-pentamethyldipropylenetriamine, N,N,N',N'-tetramethylguanidine, 1,3,5-tris(N,N-dimethylaminopropyl)hexahydro-5-triazine, 1,8-diazabicyclo[5.4.0]undecene-7, N,N,N',N'-tetramethylhexamethylenediamine, N,N'-dimethylpiperazine, dimethylcyclohexylamine, N-methylmorpholine, N-ethylmorpholine, bis(2-dimethylaminoethyl)ether, 1-methylimidazole, 1,2-dimethylimidazole, 1-isobutyl-2-methylimidazole or 1-dimethylaminopropylimidazole, may be mentioned.

The quaternary ammonium salt catalyst may be a conventional one and is not particularly limited. For example, a tetraalkylammonium halide such as tetramethylammonium chloride, a tetraalkylammonium hydroxide such as tetramethylammonium hydroxide, or a tetraalkylammonium organic acid salt such as tetramethylammonium 2-ethylhexanoate, 2-hydroxypropyltrimethylammonium formate or 2-hydroxypropyltrimethylammonium 2-ethylhexanoate, may be mentioned.

As mentioned above, in the process of the present invention, the catalyst for producing a polyurethane resin of the present invention may be used alone or as mixed with the above-mentioned other catalysts. When they are to be mixed and prepared for use, a solvent may be employed, if necessary.

Such a solvent is not particularly limited and may, for example, be an organic solvent, e.g. an alcohol such as ethylene glycol, diethylene glycol, dipropylene glycol, propylene glycol, butanediol or 2-methyl-1,3-propanediol, a hydrocarbon such as toluene, xylene, mineral turpentine or mineral spirits, an ester such as ethyl acetate, butyl acetate, methyl glycol acetate or cellosolve acetate, a ketone such as methyl ethyl ketone, methyl isobutyl ketone or cyclohexanone, or an amide such as N,N-dimethylformamide or N,N-dimethylacetamide, a chelating solvent represented by a β-diketone such as acetyl acetone or its fluorinated substitution product, or a ketoester such as methyl acetoacetate or ethyl acetoacetate, or water.

The amount of the solvent is not particularly limited but is preferably at most 3 times by weight to the total amount of the catalysts. If it exceeds 3 times by weight, it may present an influence over the physical properties of the obtainable foam, and such an excess amount is undesirable also from the economical viewpoint.

In the process of the present invention, the catalyst composition thus prepared, may be added to the polyol, or individual components may separately be added to the polyol, without any particular restriction.

In the process of the present invention, the amount of the catalyst to be used, is usually within a range of from 0.01 to 30 parts by weight, preferably from 0.1 to 20 parts by weight, per 100 parts by weight of the polyol to be used. If it is less than 0.01 part by weight, the effects of the catalyst may not be obtainable. On the other hand, if it exceeds 30 parts by weight, not only the additional effects by an increase of the catalyst may not be obtainable, but also the physical properties of the obtainable polyurethane resin may thereby be deteriorated.

In the process of the present invention, a blowing agent may be used, if necessary. The blowing agent is not particularly limited and may, for example, be a Freon-type compound such as 1,1-dichloro-1-fluoroethane (HCFC-141b), 1,1,1,3,3-pentafluoropropane (HFC-245fa), 1,1,1,3,3-pentafluorobutane (HFC-365mfc), 1,1,2-tetrafluoroethane (HFC-134a) or 1,1,1,2,3,3,3-heptafluoropropane (HFC-227ea), a hydrofluoro ether such as HFE-254pc, a low boiling point hydrocarbon, water, liquefied carbon dioxide gas, dichloromethane, formic acid or acetone. They may be used alone or in combination as a mixture of two or more of them. As the low boiling hydrocarbon, a hydrocarbon having a boiling point of from −30 to 70° C. is usually employed, and its specific examples may, for example, be propane, butane, pentane, cyclopentane, hexane, a mixture thereof, etc.

The amount of the blowing agent to be used, is determined depending upon the desired density or physical properties of the foam and is not particularly limited, and usually, it is selected so that the density of the obtainable foam becomes to be within a range of usually from 5 to 1,000 kg/m$^3$, preferably within a range of from 10 to 500 kg/m$^3$.

In the process of the present invention, a surfactant may be used as a surfactant, if necessary. The surfactant to be used, may, for example, be a conventional organic silicone type surfactant, and specifically, a nonionic surfactant such as an organic siloxane/polyoxyalkylene copolymer or a silicone/grease copolymer, or their mixture may, for example, be exemplified. The amount of the surfactant is usually from 0.1 to 10 parts by weight, preferably from 0.1 to 2 parts by weight, per 100 parts by weight of the polyol.

In the process of the present invention, a cross-linker or a chain extender may be used, if necessary. As such a cross-linker or a chain extender, for example, a low molecular weight polyhydric alcohol, such as ethylene glycol, 1,4-butanediol or glycerin, a low molecular weight amine-polyol such as diethanolamine or triethanolamine, or a polyamine such as ethylenediamine, xylylenediamine or methylenebisorthochloroaniline, may be mentioned.

In the process of the present invention, a flame retardant may be used, if necessary. The flame retardant to be used, may, for example, be a reactive flame retardant like a phosphorus-containing polyol such as propoxylated phosphoric acid or propoxylated dibutylpyrophosphoric acid obtainable by an addition reaction of phosphoric acid and an alkylene oxide, a tertiary phosphate such as tricresyl phosphate, a halogenated tertiary phosphate such as tris(2-chloroethyl)phosphate or tris(chloropropyl)phosphate, a halogen-containing organic compound such as dibromopropanol, dibromoneopentyl glycol or tetrabromobisphenol A, or an inorganic compound such as antimony oxide, magnesium carbonate or aluminum phosphate. Its amount is not particularly limited and may vary depending upon the desired flame retardancy. Usually, however, it is preferably from 4 to 20 parts by weight per 100 parts by weight of the polyol.

In the process of the present invention, a colorant, an antioxidant and other conventional additives may be used, if necessary. The types and amounts of such additives are preferably within usual ranges of the additives to be used.

The process of the present invention is carried out usually by rapidly mixing and stirring a mixed liquid having the above materials mixed and then, injecting it into a suitable container or mold to carry out foaming and molding. The mixing and stirring may be conducted by means of a common stirrer or a specialized polyurethane foaming machine. As the polyurethane foaming machine, a high pressure, low pressure or spray-type instrument may, for example, be used.

The polyurethane resin product obtainable by the process of the present invention may, for example, be an elastomer not using a blowing agent, or a polyurethane foam using a blowing agent. The process of the present invention is suitably used for the production of such a polyurethane foam product.

The polyurethane foam product may, for example, be a flexible polyurethane foam, a semi-rigid polyurethane foam or a rigid polyurethane foam. Specifically, the process of the present invention is particularly useful for the production of car seats of flexible polyurethane foam, instrument panels or steering wheels made of semi-rigid polyurethane foam to be used as automobile interior parts, or heat-insulating materials made of rigid polyurethane foam.

In the present invention, the flexible polyurethane foam is usually meant for a reversibly deformable foam having an open cell structure and a high air flow property [see Gunter Oertel, "Polyurethane Handbook" (1985 edition), Hanser Publishers (Germany), p. 161-233, or Keiji Iwata, "Polyurethane Resin Handbook", (First edition in 1987), Nikkan Kogyo Shimbun, Ltd., p. 150-221]. The physical properties of the flexible polyurethane foam is not particularly limited. Usually, however, the density is within a range of from 10 to 100 $kg/m^3$, the compression strength (ILD25%) is within a range of 200 to 8,000 kPa, and the elongation is within a range of from 80 to 500%.

The semi-rigid polyurethane foam is meant for a reversibly deformable foam having an open cell structure and a high air flow property like the flexible polyurethane foam although the foam density and compression strength are higher than the flexible polyurethane foam [see Gunter Oertel, "Polyurethane Handbook" (1985 edition), Hanser Publishers (Germany), p. 223-233, or Keiji Iwata, "Polyurethane Resin Handbook", (First edition in 1987), Nikkan Kogyo Shimbun, Ltd., p. 211-221]. Further, the polyol and isocyanate materials to be used, are also the same as for the flexible polyurethane foam, and therefore, it is usually classified into a flexible polyurethane foam. The physical properties of the semi-rigid urethane foam is not particularly limited. Usually, however, the density is within a range of from 40 to 800 $kg/m^3$, the compression strength (ILD25%) is within a range of 10 to 200 kPa, and the elongation is within a range of from 40 to 200%. In the present invention, the flexible polyurethane foam may sometimes include a semi-rigid polyurethane foam from the viewpoint of raw materials used and physical properties of the foam.

Whereas, the rigid polyurethane foam is meant for a non-reversibly deformable foam having a highly cross-liked closed-cell structure [see Gunter Oertel, "Polyurethane Handbook" (1985 edition), Hanser Publishers (Germany), p. 234-313, or Keiji Iwata, "Polyurethane Resin Handbook", (First edition in 1987), Nikkan Kogyo Shimbun, Ltd., p. 224-283]. The physical properties of the rigid urethane foam is not particularly limited. Usually, however, the density is within a range of from 10 to 100 $kg/m^3$, and the compression strength (ILD25%) is within a range of 50 to 1,000 kPa.

EXAMPLES

The present invention will be described in further detail with reference to the following Examples. However, it should be understood that the present invention is by no means thereby restricted.

The analytical instruments and measuring methods employed in these Examples are as follows.

[Elemental Analysis]
  Elemental analyzer: PerkinElmer full automatic elemental analyzer 2400II
  Oxygen flask combustion-IC measuring method: Ion Chromatograph IC-2001, manufactured by Tosoh Corporation
[NMR (Nuclear Magnetic Resonance) Measurement]
  NMR measuring apparatus 1: VARIAN Gemini-200
  NMR measuring apparatus 2: VARIAN VXR-300S
  In all NMR measurements other than in Reference Example 3, NMR measuring apparatus 2 was used.
[GC-MS (Gas Chromatograph Mass Spectrometry)]
  Mass spectrometer: JMS-K9, manufactured by JEOL Ltd.
  Measuring method: Column DB-5, manufactured by Agilent Technologies
  Column temperature 100° C.→300° C. (10° C./min., after the temperature rise, the temperature is held for 20 minutes)
  Inlet temperature=detector temperature=280° C.
  Injected amount=0.2 microlitter Reference Example 1 (Preparation of Catalyst 1 for Gas Phase Reaction)

40 g of commercially available aluminum phosphate (manufactured by Kishida Chemical Co., Ltd.) was mixed to 300 ml of water to obtain a slurry solution, and then, 2.4 g (metal ratio: 10 mol %) of sodium sulfate (manufactured by Kishida Chemical Co., Ltd.) dissolved in 100 ml of water, was mixed, followed by dehydration by means of an evaporator to obtain 44.1 g of a white solid. To this solid, 0.42 g (1 wt %) of graphite was added, followed by tableting by means of a tableting machine to obtain a tablet having a diameter of 5 mm and a thickness of 2 mm. This tablet was fired in a muffle furnace under conditions of 450° C. for 6 hours to obtain catalyst 1 for gas phase reaction.

Reference Example 2 (Preparation of Catalyst 2 for Gas Phase Reaction)

Catalyst 2 for gas phase reaction was obtained in the same manner as in Reference Example 1 except that in Reference Example 1, instead of 2.4 g of sodium sulfate (manufactured by Kishida Chemical Co., Ltd.), 6.4 g (metal ratio: 10 mol %) of cesium nitrate (manufactured by Wako Pure Chemical Industries, Ltd.) was used.

Reference Example 3 [Synthesis of 3-(1'-piperazinyl)-1,2-propanediol (DHPP)]

Into a 500 ml three neck flask, 172.3 g (2.0 mol) of piperazine and 220 ml of methanol as a solvent, were charged, and 44.4 g (0.6 mol) of glycidol was dropwise added in a nitrogen atmosphere over a period of 4 hours. In an oil bath, the three neck flask was adjusted so that the reaction temperature became 60° C. After completion of the dropwise addition of glycidol, the flask was taken out from the oil bath and cooled to terminate the reaction. The reaction solution was subjected to simple distillation to distil off methanol as the solvent in the reaction solution and unreacted piperazine, followed by distillation under reduced pressure to isolate the desired product (white solid, amount: 88.3 g, yield: 92%). From the analyses by GC-MS and NMR, it was confirmed to be DHPP represented by the following formula (3):

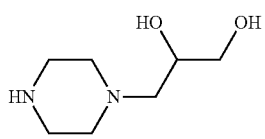

(3)

GC-MS:m/z=160.
$^{13}$C-NMR (CDCl$_3$, internal standard tetramethylsilane (hereinafter TMS)): 66.71, 64.97, 61.16, 54.64, 46.04.

Reference Example 4 [Synthesis of 3-(3'-methylpiperazin-1'-yl)-1,2-propanediol (DHPMP)]

A slightly yellowish oily substance was obtained (amount: 68.0 g, yield: 65%) in the same manner as in Reference Example 3 except that in Reference Example 3, instead of 172.3 g (2.0 mol) of piperazine, 200.3 g (2.0 mol) of 2-methylpiperazine was used. From the analyses by GC-MS and NMR, it was confirmed to be a mixture of 3-(3'-methylpiperazin-1'-yl)-1,2-propanediol (DHPMP) represented by the following formula (4) and 3-(2'-methylpiperazin-1'-yl)-1,2-propanediol represented by the following formula (5):

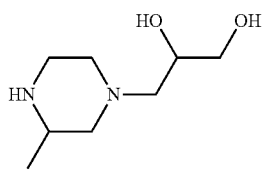

(4)

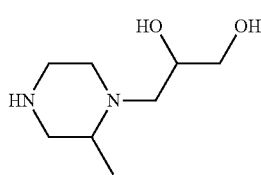

(5)

GC-MS:m/z=174.
$^{13}$C-NMR (CDCl$_3$, internal standard TMS): 66.60, 64.95, 62.66, 60.76, 60.67, 60.34, 55.03, 52.76, 50.81, 50.61, 46.05, 45.91, 19.89.

Example 1 Synthesis (1) of Compound Represented by Exemplified Compound No. 1-1

Figure 2:
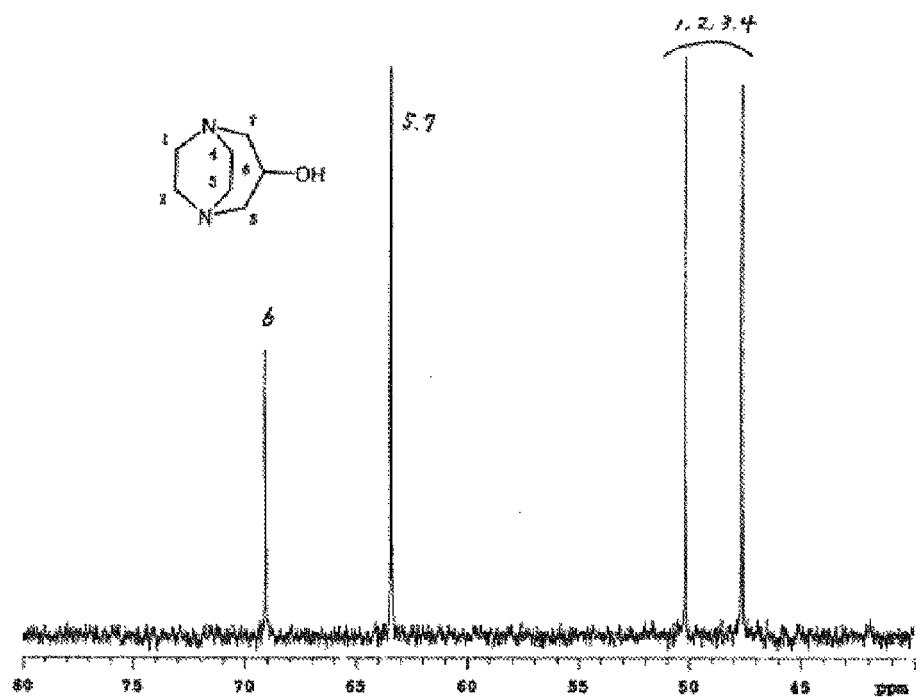
FIG. 2 shows the $^{13}$C-NMR spectrum of a compound identified by exemplified compound No. 1-1.
Figure 3:
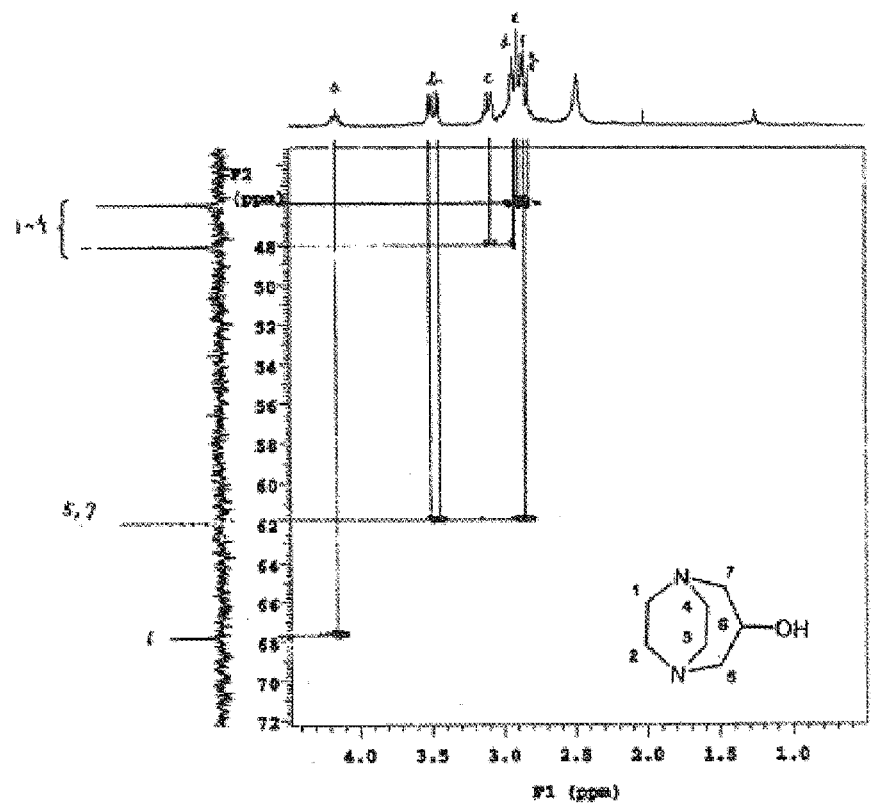
FIG. 3 shows the $^1$H-$^{13}$C COSY-NMR spectrum of a compound identified by exemplified compound No. 1-1.

At a center portion of a quartz glass tube having an inner diameter of 20 mm, 20 ml of catalyst 1 for gas phase reaction prepared in Reference Example 1 was packed, and at upper and lower portions thereof, Raschig rings having an outer diameter of 3 mm were packed. While maintaining the catalyst layer and the Raschig ring layers at 340° C. by an electric furnace, an aqueous solution (2 mol %) of 80.1 g (0.50 mol) of DHPP obtained in Reference Example 3 was dropwise added from the upper portion at a rate of GHSV (gas hourly space velocity)=1,500 Hr$^{-1}$. Further, as a diluent gas, nitrogen gas was entrained at a rate of GHSV=750 Hr$^{-1}$. After 3 hours from the initiation of feeding, the reaction liquid was sampled over one hour and analyzed by gas chromatography (column: DB-5, manufactured by Agilent Technologies, column temperature: 100° C.→280° C., 10° C./min., held for 12 minutes after temperature rise), whereby the conversion of DHPP was 96%. The obtained component was analyzed by GC-MS, distilled and isolated by column chromatography, and then analyzed by NMR and the elemental analysis, whereby it was confirmed to be 3-hydroxy-1,5-diazabicyclo[3.2.2]nonane represented by the above-mentioned exemplified compound No. 1-1. The yield was 3%. The measurement results of the elemental analysis, 1H-NMR, $^{13}$C-NMR and $^1$H-$^{13}$C COSY-NMR are shown in Table 1, FIG. 1, FIG. 2 and FIG. 3, respectively.

TABLE 1

|  | C | H | N |
|---|---|---|---|
| Measured values (wt %) | 59.0 | 10.0 | 19.6 |
| Theoretical values (wt %) | 59.1 | 9.9 | 19.7 |

GC-MS:m/z=142.
$^1$H-NMR (CDCl$_3$, internal standard TMS): 4.1-4.2 (1H; m), 3.47 (2H; dd; 14.5, 6.0 Hz), 3.7-3.2 (10H; m).
$^{13}$C-NMR (D$_2$O, internal standard sodium trimethylsilyl propionate): 69.09, 63.46, 50.20, 47.66.

Example 2 Synthesis (2) of Compound Represented by Exemplified Compound No. 1-1

The synthesis was carried out in the same manner as in Example 1, except that in Example 1, instead of catalyst 1 for gas phase reaction, catalyst 2 for gas phase reaction prepared in Reference Example 2 was used, and the temperature of the catalyst layer and the Raschig ring layer was maintained at 360° C. The product was analyzed by gas chromatography, whereby the conversion of DHPP was 100%, and the yield of the compound represented by the above-mentioned exemplified compound No. 1-1 was 7%.

Example 3 Synthesis of Compound Represented by Exemplified Compound No. 1-2

The synthesis was carried out in the same manner as in Example 2, except that in Example 2, instead of 80.1 g (0.50 mol) of DHPP prepared in Reference Example 3, 61 g (0.35 mol) of DHPMP prepared in Reference Example 4 was used.
The product was analyzed by gas chromatography, whereby the conversion of DHPMP was 100%. The obtained component was analyzed by GC-MS, distilled and isolated by column chromatography, and then analyzed by NMR and the elemental analysis, whereby it was confirmed to be 3-hydroxy-6-methyl-1,5-diazabicyclo[3.2.2]nonane represented by the above-mentioned exemplified compound No. 1-2. The yield was 5%. The measurement results of the elemental analysis are shown in Table 2.

TABLE 2

|  | C | H | N |
|---|---|---|---|
| Measured values (wt %) | 61.4 | 10.4 | 17.8 |
| Theoretical values (wt %) | 61.5 | 10.3 | 17.9 |

GC-MS:m/z=156.

Example 4 Synthesis of Compound Represented by Exemplified Compound No. 1-6

3-(3'-Hydroxymethylpiperazin-1'-yl)-1,2-propanediol (DHPHMP) represented by the following formula (6):

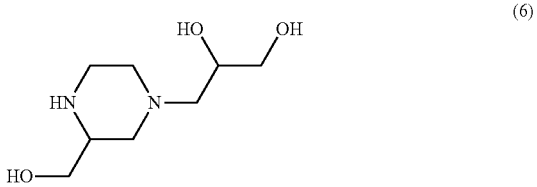 [SMILES: OCC(O)CN1CCNC(CO)C1]

(6)

was synthesized in the same manner as in Reference Example 3 except that in Reference Example 3, instead of 172.3 g (2.0 mol) of piperazine, 232.3 g (2.0 mol) of 2-hydroxymethylpiperazine prepared by the method disclosed in JP-A-2011-42587, was used.

Here, in this substance, 3-(2'-hydroxymethylpiperazin-1'-yl)-1,2-propanediol represented by the following formula (7):

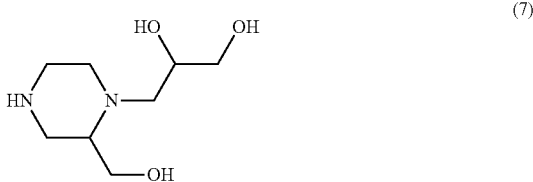 [SMILES: OCC(O)CN1CCNCC1CO]

(7)

was also contained as an isomer.

Then, the synthesis was carried out in the same manner as in Example 2 except that in Example 2, instead of DHPP, DHPHMP was used.

As a result of the analysis by gas chromatography, the conversion of DHPHMP was 96%. The obtained component was analyzed by GC-MS, distilled and isolated by column chromatography, and then analyzed by NMR and the elemental analysis, whereby it was confirmed to be 3-hydroxy-6-hydroxymethyl-1,5-diazabicyclo[3.2.2]nonane represented by the above-mentioned exemplified compound No. 1-6. The yield was 3%.

Example 5 and Comparative Examples 1 to 3

Examples will be given below in which flexible high resilience polyurethane foams were produced by using a cyclic amine compound of the present invention and catalysts of Comparative Examples.

3-Hydroxy-1,5-diazabicyclo[3.2.2]nonane (exemplified compound No. 1-1) synthesized in Example 2 was diluted with dipropylene glycol (DPG) to 33.3 wt % to prepare catalyst solution 1. Likewise, 1,5-diazabicyclo[3.2.2]nonane and 1,4-diazabicyclo[2.2.2]octane were, respectively, diluted with dipropylene glycol to 33.3 wt % to prepare catalyst solution 2 and catalyst solution 3, respectively. Further, as a reactive catalyst, N,N-dimethyl-N',N'-bis(hydroxypropyl)propanediamine (DMAPA2PO) was used directly as catalyst solution 4.

The polyol, water, the cross-linker and the surfactant were mixed in a raw material blend ratio as shown in Table 3 to prepare premix A. 83.9 g of premix A was put into each of four 300 ml polyethylene cups. Further, catalyst solutions 1, 2, 3 and 4 were, respectively, added in such an amount that the reactivity would be 35±1 seconds by the following gel time, and the temperature of each solution was adjusted to 20° C. Then, a polyisocyanate liquid (Coronate 1106, manufactured by Nippon Polyurethane Industry Co., Ltd.) having the temperature adjusted to 20° C. in a separate container, was put into each of the cups of premix A in such an amount that the isocyanate index (isocyanate group/OH group (molar ratio)×100) would be 100 and quickly stirred at 6,000 rpm for 5 seconds by a stirrer. Thereafter, each mixed liquid thus mixed and stirred, was transferred to a 2 L (liter) polyethylene cup having the temperature adjusted to 60° C., and the reactivity during foaming was measured. Then, by increasing the amounts of the raw materials, in a similar operation, into a mold (made of aluminum and having internal dimensions of 35 cm×35 cm×10 cm) having the temperature adjusted to 60° C., the mixed liquid was introduced so that the over-all density of the foam would be 51 kg/m³, and, after putting a lid, foamed and molded. After 5 minutes from the time when the mixed liquid was introduced, the foam was removed from the mold. With respect to the molded foam, the over-all density of the foam, the amine catalyst volatilization amount and the foam odor were measured and compared. The results are shown in Table 4.

TABLE 3

| | Parts by weight (pbw) |
|---|---|
| Polyol A [1] | 98 |
| Polyol B [2] | 2 |
| Diethanolamine [3] | 0.65 |
| Water | 3.2 |
| Surfactant A [4] | 1 |
| Polymeric MDI [5] | Isocyanate INDEX 100 [6] |

[1] FA-703, polyether polyol manufactured by Sanyo Chemical Industries, Ltd. (OH value = 34 mgKOH/g)
[2] CP1421, polyol manufactured by Dow Chemical (OH value = 35 mgKOH/g)
[3] Cross-linker manufactured by Wako Pure Chemical Industries, Ltd.
[4] B4113, silicone-type surfactant manufactured by Goldschmidt
[5] Coronate 1106 manufactured by Nippon Polyurethane Industry Co., Ltd. (NCO amount: 31.8%)
[6] INDEX = (molar amount of NCO groups/molar amount of OH groups) × 100

TABLE 4

| | | Ex. 5 | Comp. Ex. 1 | Comp. Ex. 2 | Comp. Ex. 3 |
|---|---|---|---|---|---|
| Amount of catalyst (pbw) | | | | | |
| Catalyst solution 1 [a] | | 3.43 | | | |
| Catalyst solution 2 [b] | | | 1.75 | | |
| Catalyst solution 3 [c] | | | | 1.55 | |
| Catalyst solution 4 [d] | | | | | 2.79 |
| Catalyst activities | | ○ | ◎ | ◎ | △ |
| Reactivity (sec) | | | | | |
| Cream time | | 11 | 9 | 10 | 11 |
| Gel time | | 35 | 35 | 35 | 36 |
| Rise time | | 51 | 52 | 51 | 50 |
| Physical properties of foam | | | | | |
| Over-all density | (kg/m³) | 51.4 | 50.8 | 50.5 | 51.3 |
| Amine catalyst volatilization amount (VOC) | (ppm) | 9 | 1,266 | 1,145 | 11 |
| Amine catalyst volatilization amount (Fogging) | (pm) | 56 | 668 | 604 | 67 |

[a] DPG solution of 3-hydroxy-1,5-diazabicyclo[3.2.2]nonane (33.3 wt %)
[b] DPG solution of 1,5-diazabicyclo[3.2.2]nonane (33.3 wt %)
[c] DPG solution of 1,4-diazabicyclo[2.2.2]octane (33.3 wt %)
[d] N,N-dimethyl-N',N'-bis(hydroxypropyl)propanediamine (DMAPA2PO)

The methods for measurement of the respective measured items are as follows.

(1) Measured Items of the Reactivity

Cream time: The foaming initiation time and the time at the initiation of the rising of the foam were visually measured.

Gel time: As the reaction proceeded, the time when the liquid material turned into a resinous material was measured.

Figure 4:
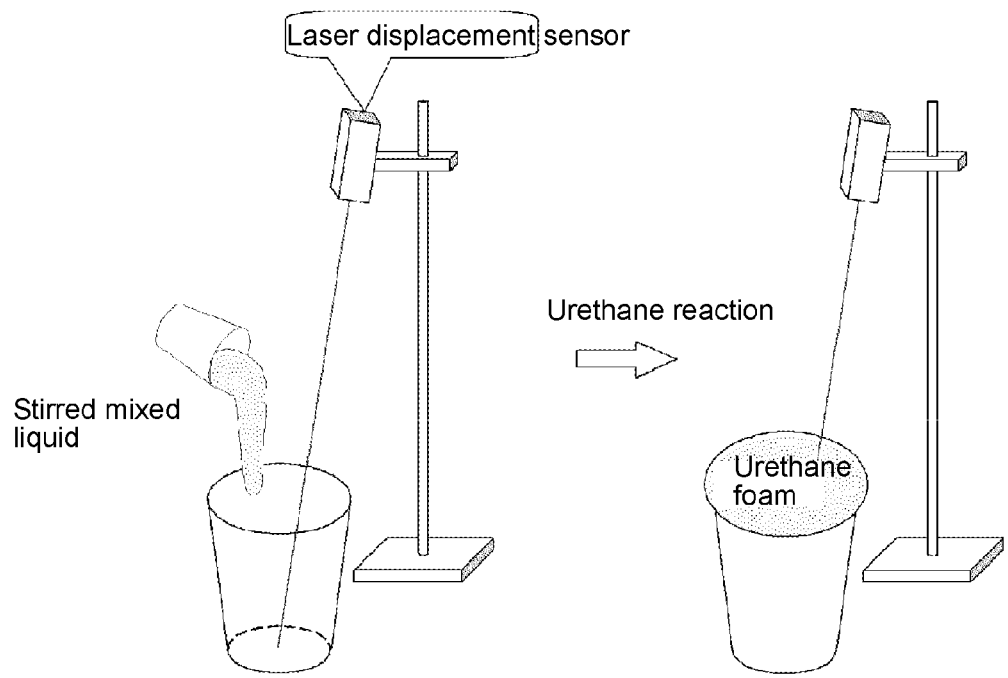
FIG. 4 shows the method for measuring the rise profile in Examples.

Rise time: The time when the rising of the foam had terminated, was measured by means of a displacement sensor (Model: LF-2510, manufactured by Keyence Corporation) (FIG. 4).

Catalytic activity: Using Comparative Example 1 as the standard, the amount of each catalyst composition used was compared and evaluated as follows.

⊚: Amount used decreased substantially

Figure 5:
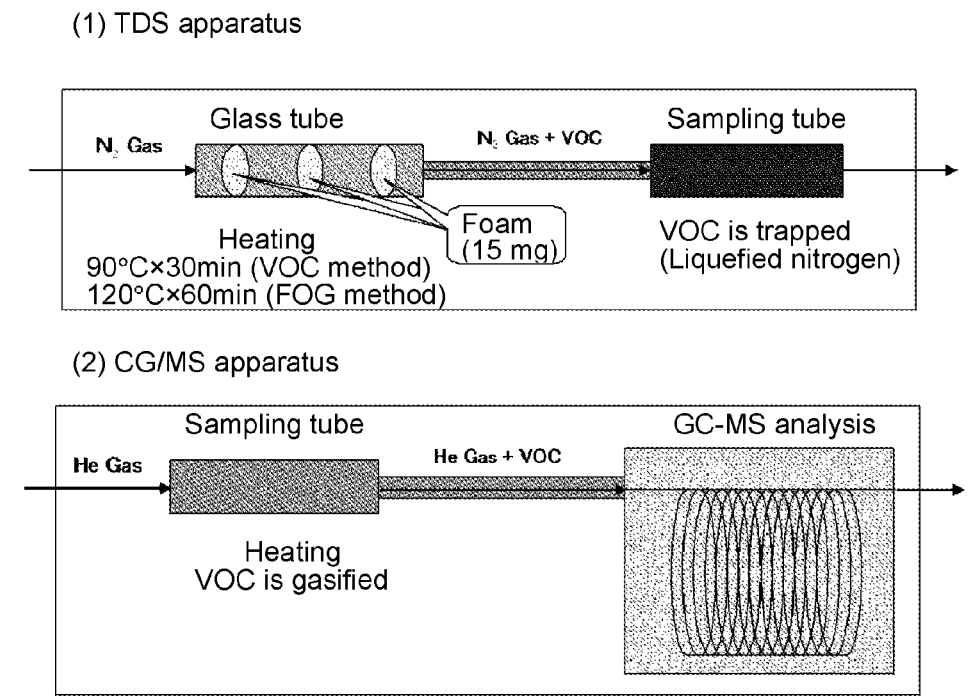
FIG. 5 shows the method for measuring a volatile organic compound (VOC) in Examples.

◯: Amount used decreased x: Amount used increased (2) Amine Catalyst Volatilization Amount The amount of the amine catalyst volatilizing from the foam was quantitatively determined by condensation in accordance with the method of VDA-278. That is, a foam formed by an aluminum mold was aged for one day, and then, 15 mg of the foam was cut out to include the skin layer, put into a glass tube and heated at 90° C. for 30 minutes by a temperature-programmed desorbed gas analyzer (TDS, manufactured by Gerstel, Model: TDS-2A) to have the volatile organic compound (VOC) in the foam desorbed and collected in a sampling tube [FIG. 5 (1)]. Then, this sampling tube was heated, and VOC gas was injected into a gas chromatograph mass spectrometer (GC-MS, manufactured by Agilent Technologies, Model: HP6890/5973), whereupon the VOC amount was measured [FIG. 5 (2)] For the quantitative determination of the VOC amount, a qualitative analysis of a peak from a retention time (mass analysis retention time) of the mass spectrum was carried out, and in a case where a target component for quantitative determination was detected, the quantity was determined by calculation of the proportionality to the peak area value of each standard substance. Continuously, this foam was heated at 120° C. for 60 minutes to have a misty substance (Fogging) in the foam desorbed and collected, whereupon in the same manner as for the measurement of the VOC amount, the Fogging amount was quantitatively determined. With respect to each volatilization amount, the quantitative amount value was represented by the amount (ppm) of the amine catalyst per 1 g of the foam.

As shown by Example 5, it has been made evident that 3-hydroxy-1,5-diazabicyclo[3.2.2]nonane having a hydroxy group introduced is useful for the production of a polyurethane resin. Further, as is evident from the comparison with Comparative Example 1, it was possible to reduce the volatile amine component in the foam to a large extent, as compared with 1,5-diazabicyclo[3.2.2]nonane. On the other hand, with respect to the catalytic activity, since it is a reactive catalyst, the catalytic activity is low as compared with a non-reactive catalyst, but as a pure amine component, the catalytic activity is high as compared with DMAPA2PO of Comparative Example 3. Thus, it has been confirmed that the cyclic amine compound of the present invention is useful for the production of a polyurethane resin.

Preparation Example 1 (Synthesis of Compound Represented by Exemplified Compound No. 2-1)

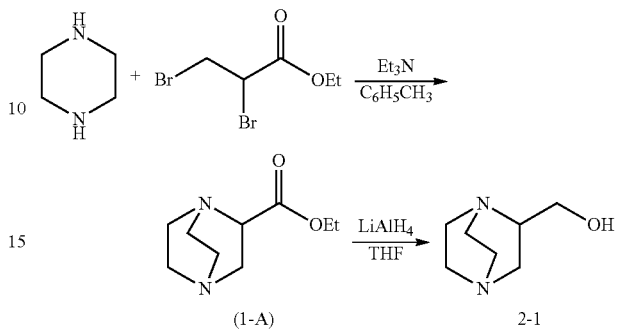

Into a 2 L separable flask, 43.1 g (0.5 mol) of piperazine and 151.8 g (1.5 mol) of triethylamine were charged and diluted with 1,000 ml of toluene. After nitrogen substitution, 131.9 g (0.5 mol) of ethyl 2,3-dibromopropionate (manufactured by Tokyo Chemical Industry Co., Ltd.) diluted with 500 ml of toluene, was added thereto with stirring, followed by heating and reaction at 100° C. for 24 hours.

Figure 6:
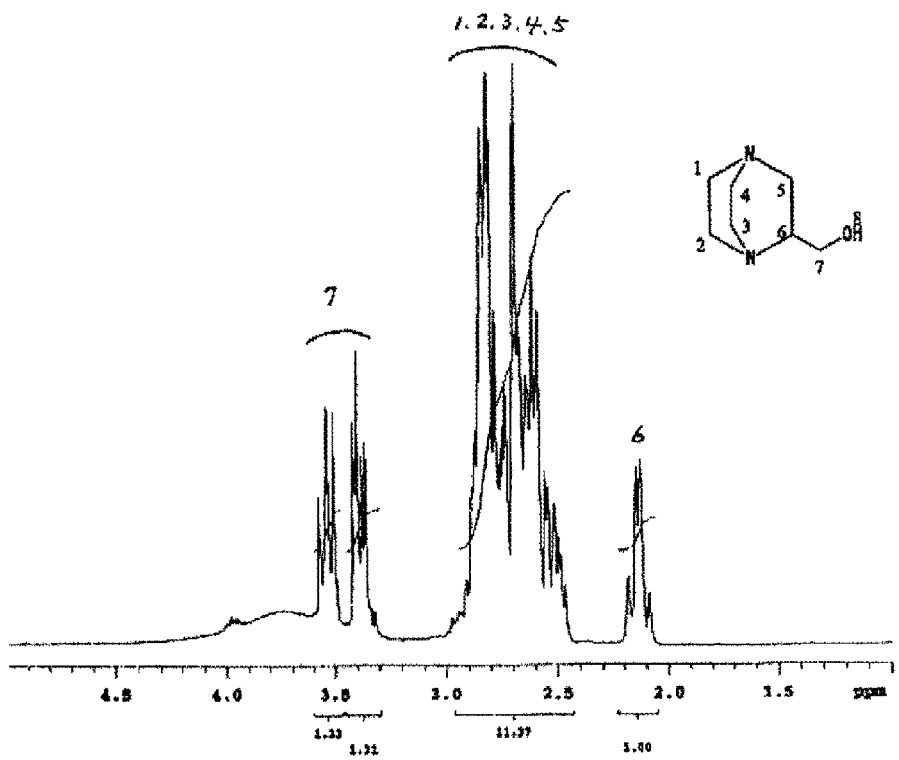
FIG. 6 shows the $^1$H-NMR spectrum of a compound identified by exemplified compound No. 2-1.
Figure 7:
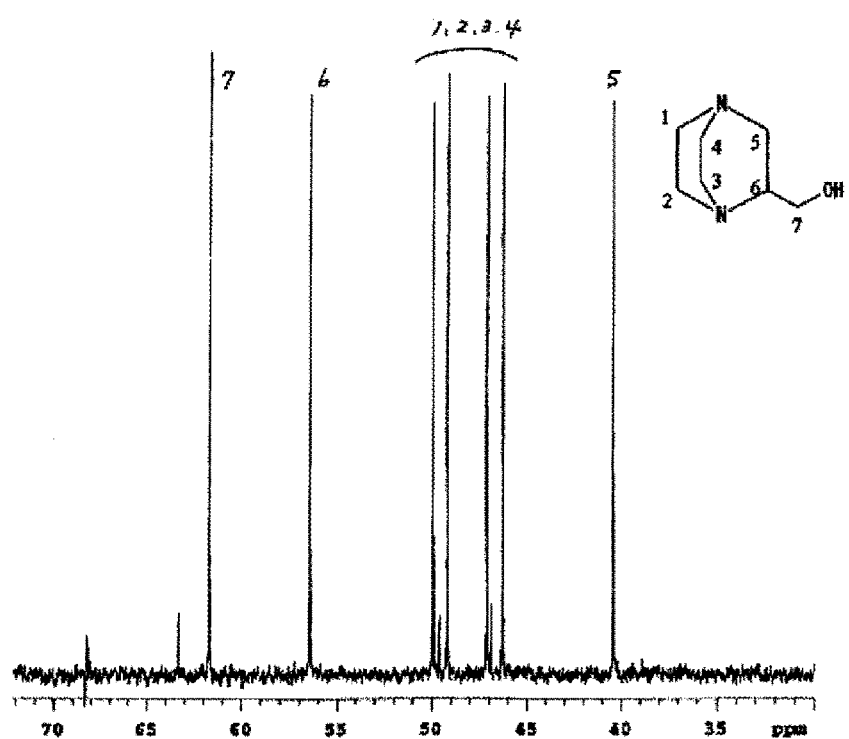
FIG. 7 shows the $^{13}$C-NMR spectrum of a compound identified by exemplified compound No. 2-1.

The precipitated HBr salt of triethylamine was removed by filtration, and the obtained reaction liquid was concentrated under reduced pressure to obtain an ester compound (1-A). This ester compound was dissolved in 500 ml of tetrahydrofuran and, in an ice bath, added to 1,000 ml of a tetrahydrofuran solution of 19.0 g (0.5 mol) of lithium aluminum hydride with stirring slowly. After the reaction at room temperature for 2 hours, 19 ml of water and a 15 wt % sodium hydroxide aqueous solution (19 ml) were added to terminate the reaction, whereupon any insoluble was removed by filtration. The reaction liquid was concentrated, then extracted with ethyl acetate and washed. After removing ethyl acetate under reduced pressure, recrystallization was carried out by using tetrahydrofuran to obtain 48 g (yield: 68%) of a slightly yellow solid as the desired compound. This solid was analyzed by the elemental analysis and NMR, whereby it was confirmed to be 1,4-diazabicyclo[2.2.2]octane-2-methanol represented by the abovementioned exemplified compound No. 2-1. The measurement results of the elemental analysis, $^1$H-NMR and $^{13}$C-NMR spectrum are shown in Table 5, FIG. 6 and FIG. 7, respectively.

TABLE 5

|  | C | H | N |
|---|---|---|---|
| Measured values (wt %) | 59.3 | 9.8 | 19.4 |
| Theoretical values (wt %) | 59.1 | 9.9 | 19.7 |

GC-MS:m/z=142.

$^1$H-NMR (CDCl$_3$, internal standard TMS): 3.3-3.6 (2H; m), 2.5-3.1 (10H; m), 2.3 (1H; m).

$^{13}$C-NMR (CDCl$_3$, internal standard TMS): 61.51, 56.25, 49.94, 49.24, 47.21, 46.40, 40.32.

Preparation Example 2 (Synthesis of Compound Represented by Exemplified Compound No. 1-1)

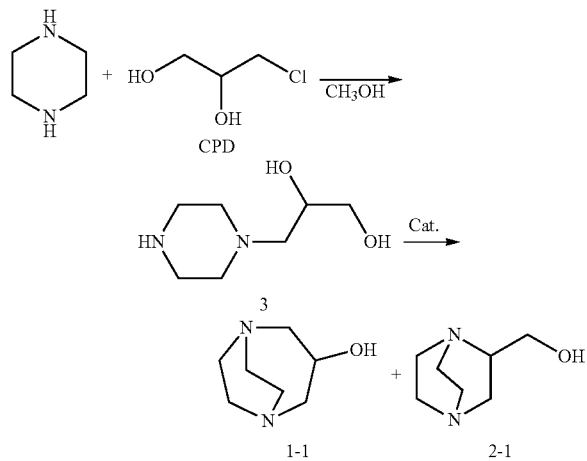

Into a 50 L reactor, 15.5 kg (180 mol) of piperazine and 15.6 L of methanol as a solvent were charged and adjusted in a nitrogen atmosphere so that the liquid temperature became 45° C., and then, 6.06 kg (54.8 mol) of 3-chloro-1,2-propanediol was dropwise added over a period of 3 hours. During the dropwise addition, the liquid temperature gradually rose, and the liquid temperature at the termination of the dropwise addition was 75° C. Thereafter, the reaction temperature was adjusted to be 70° C., followed by ageing for further 3 hours. The conversion was 100%. The reaction liquid was left to stand still over night to cool to the vicinity of room temperature, and 4.6 kg (55 mol) of a 48 wt % sodium hydroxide aqueous solution was slowly dropwise added thereto to have a by-product salt precipitated. The reaction liquid withdrawn from the bottom of the reactor was desalinated by filtration treatment, and then, methanol was distilled off by means of an evaporator. Further, unreacted piperazine was distilled off by simple distillation, followed by distillation under reduced pressure to isolate the desired product (white solid, obtained amount: 7.9 kg, yield: 90%). From the analyses of GC-MS and NMR, it was confirmed to be 3-(1'-piperazinyl)-1,2-propanediol (3). These measurement results are shown below.

GC-MS:m/z=160.

$^{13}$C-NMR (CDCl$_3$): 66.71, 64.97, 61.16, 54.64, 46.04.

At a center portion of a quartz glass tube having an inner diameter of 40 mm, 160 ml of catalyst 1 for gas phase reaction prepared in Reference Example 1 was packed, and at upper and lower portions thereof, Raschig rings having an outer diameter of 5 mm were packed. While maintaining the catalyst layer and the Raschig ring layers at 360° C. by an electric furnace, a 2 mol % aqueous solution of 1.6 kg (10 mol) of 3-(1'-piperazinyl)-1,2-propanediol represented by the above formula (3) was dropwise added from the upper portion at a rate of GHSV=1,500 Hr$^{-1}$. Further, as a diluent gas, nitrogen gas was entrained at a rate of GHSV=750 Hr$^{-1}$. After 3 hours from the initiation of feeding, the reaction liquid was sampled over one hour and analyzed by gas chromatography (column: DB-5, manufactured by Agilent Technologies, column temperature: 100° C.→280° C., 10° C./min., held for 12 minutes after temperature rise), whereby the conversion was 100%. The obtained component was analyzed by GC-MS, then distilled and further isolated by column chromatography, and then analyzed by NMR and the elemental analysis, whereby it was confirmed to be 3-hydroxy-1,5-diazabicyclo[3.2.2]nonane represented by the above-mentioned exemplified compound No. 1-1. The yield was 6%.

Other products were 1,4-diazabicyclo[2.2.2]octane-2-methanol represented by the above-mentioned exemplified compound No. 2-1 (42%), piperazine having a side chain detached (13%) and 1,4-diazabicyclo[2.2.2]octane (1%). The measurement results of the elemental analysis, $^1$H-NMR, $^{13}$C-NMR and $^1$H-$^{13}$C COSY-NMR spectrum are shown in Table 6, FIG. 1, FIG. 2 and FIG. 3, respectively.

TABLE 6

|  | C | H | N |
|---|---|---|---|
| Measured values (wt %) | 59.0 | 10.0 | 19.6 |
| Theoretical values (wt %) | 59.1 | 9.9 | 19.7 |

Further, the results of the mass analysis and NMR measurement are shown below.

GC-MS:m/z=142.

$^1$H-NMR (CDCl$_3$): 4.1-4.2 (1H; m), 3.47 (2H; dd; 14.5, 6.0 Hz), 3.7-3.2 (10H; m).

$^{13}$C-NMR (D$_2$O): 69.09, 63.46, 50.20, 47.66.

Preparation Example 3 (Synthesis of Amine Mixture of Compound Represented by Exemplified Compound No. 1-1 and Compound Represented by Exemplified Compound No. 2-1)

Other than 1,4-diazabicyclo[2.2.2]octane-2-methanol as a compound represented by the above-mentioned exemplified compound No. 2-1 and 3-hydroxy-1,5-diazabicyclo[3.2.2]nonane as a compound represented by the above-mentioned exemplified compound No. 1-1, were fractionated by distillation from the reaction liquid obtained in Preparation Example 2, followed by recrystallization using tetrahydrofuran, to obtain about 20 g of an amine mixture (slightly yellow solid) of the compound represented by exemplified compound No. 2-1 and the compound represented by exemplified compound No. 1-1. The ratio of [compound represented by exemplified compound No. 2-1]/[compound represented by exemplified compound No. 1-1] was 7/1 by weight ratio.

Preparation Example 4 (Synthesis of Compound Represented by Exemplified Compound No. 2-8)

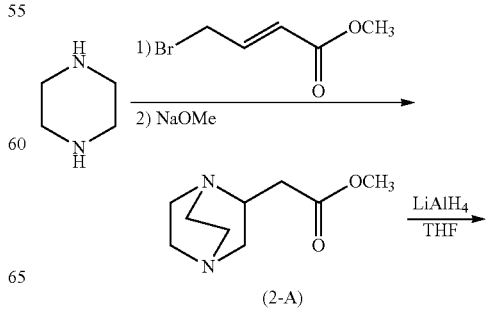

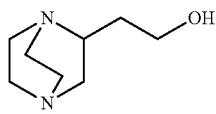

2-8

The reaction was carried out in accordance with the method disclosed in Reference Example 6 in WO95/18104.

That is, into a 1 L separable flask, 43.1 g (0.5 mol) of piperazine and 500 ml of methanol were charged, and then, 36.9 g (0.175 mol) of methyl 4-bromocrotonate (purity: 85%, manufactured by Aldrich) was slowly added with stirring, followed by heating and refluxing for 24 hours. After cooling, the precipitated HBr salt of piperazine was removed by filtration, and then, methanol was distilled off under reduced pressure. Then, this crude product was diluted with 400 ml of diethyl ether, and then, a methanol solution of sodium methoxide (30 ml of a 28 wt % solution) was added. The precipitate was removed by filtration again, and the filtrate was concentrated under reduced pressure to obtain an ester compound (2-A) as a brown oily substance. This ester compound was dissolved in 500 ml of tetrahydrofuran and added to 1,000 ml of a tetrahydrofuran solution of 19.0 g (0.5 mol) of lithium aluminum hydride in an ice bath with stirring slowly. After a reaction at room temperature for 2 hours, 19 ml of water and 19 ml of a 15 wt % sodium hydroxide aqueous solution were added to terminate the reaction, whereupon any insoluble was removed by filtration. The reaction liquid was concentrated under reduced pressure, then extracted with ethyl acetate and washed. The ethyl acetate was removed under reduced pressure, followed by recrystallization using tetrahydrofuran to obtain 50 g (yield: 64%) of a slightly yellow solid as the desired compound. From the analyses of GC-MS and NMR of the product, the product was confirmed to be 1,4-diazabicyclo[2.2.2]octane-2-ethanol represented by the above-mentioned exemplified compound No. 2-8. The results of the mass analysis are shown below.

GC-MS: m/z=156.

Preparation Example 5 (Synthesis of Amine Mixture of Compound Represented by Exemplified Compound No. 1-2 and Compound Represented by Exemplified Compound No. 2-2)

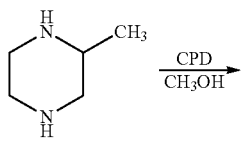

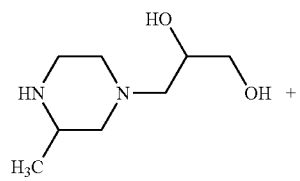

4

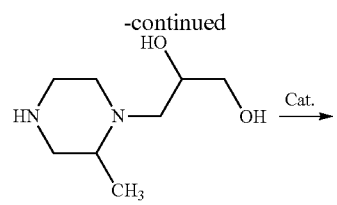

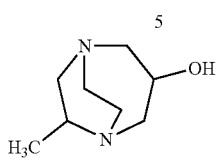

1-2　　　　　2-2

A slightly yellow oily substance was obtained (obtained amount: 6.5 kg, yield: 68%) in the same manner as in Preparation Example 2 except that in Preparation Example 2, instead of 15.5 kg (180 mol) of piperazine, 18.0 kg (180 mol) of 2-methylpiperazine was used. From the analyses of GC-MS and NMR, it was confirmed to be a mixture of 3-(3'-methylpiperazin-1'-yl)-1,2-propanediol (4) and 3-(2'-methylpiperazin-1'-yl)-1,2-propanediol (5). The results of the mass analysis and NMR are shown below.

GC-MS:m/z=174.

$^{13}$C-NMR (CDCl$_3$): 66.60, 64.95, 62.66, 60.76, 60.67, 60.34, 55.03, 52.76, 50.81, 50.61, 46.05, 45.91, 19.89.

Then, 1.7 kg (10 mol) of this mixture was formed into a 2 mol % aqueous solution, which was fed to catalyst 1 for gas phase reaction prepared in Reference Example 1 in the same manner as in Preparation Example 2. While maintaining the catalyst layer and the Raschig ring layers at 380° C. by an electric furnace and after 3 hours from the initiation of feeding, the reaction liquid was sampled over a period of 1 hour and analyzed by gas chromatography, whereby the conversion was 96%. The obtained component was analyzed by GC-MS, whereby 3-hydroxy-6-methyl-1,5-diazabicyclo [3.2.2]nonane represented by the above-mentioned exemplified compound No. 1-2 was obtained in a yield of 5%. Other products were 5-methyl-1,4-diazabicyclo[2.2.2]octane-2-methanol represented by the above-mentioned exemplified compound No. 2-2 (38%) and piperazine having a side chain detached (18%). A part of the reaction liquid passed through the catalyst layer for a predetermined period of time was fractionated by distillation to obtain about 23 g of an amine mixture (yellow oily substance) of the compound represented by exemplified compound No. 2-2 and the compound represented by exemplified compound No. 1-2. The ratio of [compound represented by exemplified compound No. 2-2]/[compound represented by exemplified compound No. 1-2] was 8/1 by weight ratio.

Preparation Example 6 (Synthesis of Amine Mixture of Compound Represented by Exemplified Compound No. 1-6 and Compound Represented by Exemplified Compound No. 2-6)

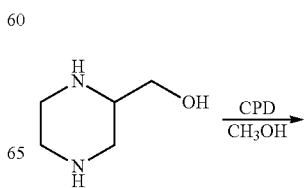

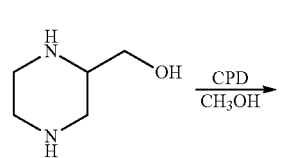

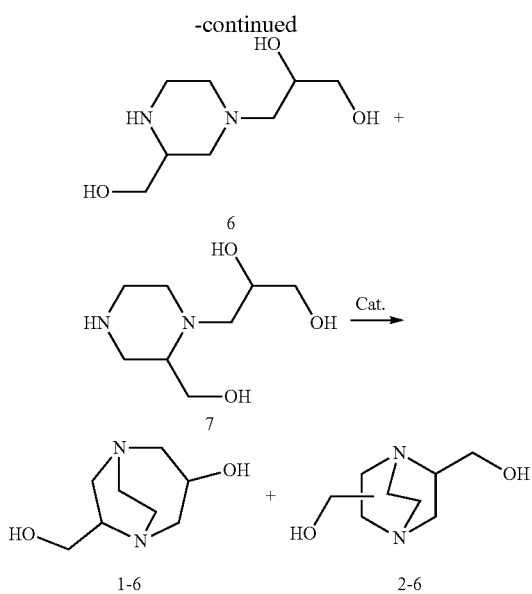

A yellow oily substance was obtained (obtained amount: 6.1 kg, yield: 59%) in the same manner as in Preparation Example 2 except that in Preparation Example 2, instead of 15.5 kg (180 mol) of piperazine, 20.9 kg (180 mol) of 2-hydroxymethylpiperazine prepared by the method disclosed in JP-A-2011-42587 was used. From the analyses of GC-MS and NMR, it was confirmed to be a mixture of 3-(3'-hydroxymethylpiperazin-1'-yl)-1,2-propanediol (6) and 3-(2'-hydroxymethylpiperazin-1'-yl)-1,2-propanediol (7).

Then, 1.9 kg (10 mol) of this mixture was formed into a 2 mol % aqueous solution, which was fed to catalyst 1 for gas phase reaction prepared in Reference Example 1 in the same manner as in Preparation Example 2. While maintaining the catalyst layer and the Raschig ring layers at 390° C. by an electric furnace and after 3 hours from the initiation of feeding, the reaction liquid was sampled over a period of 1 hour and analyzed by gas chromatography, whereby the conversion was 100%. The obtained component was analyzed by GC-MS, whereby 3-hydroxy-6-hydroxymethyl-1,5-diazabicyclo[3.2.2]nonane represented by the above-mentioned exemplified compound No. 2-6 was obtained in a yield of 4%. Other products were 5-hydroxymethyl-1,4-diazabicyclo[2.2.2]octane-2-methanol represented by the above-mentioned exemplified compound No. 1-6 (35%) and piperazine having a side chain detached (22%). A part of the reaction liquid passed through the catalyst layer for a predetermined period of time was fractionated by distillation to obtain about 18 g of an amine mixture (yellow oily substance) of the compound represented by exemplified compound No. 2-6 and the compound represented by exemplified compound No. 1-6. The ratio of [compound represented by exemplified compound No. 2-6]/[compound represented by exemplified compound No. 1-6] was 10/1 by weight ratio.

Examples 6 to 12 and Comparative Example 4

Examples will be given below in which flexible high resilience polyurethane foams were produced by using catalysts of the present invention and a catalyst of Comparative Example.

Catalyst solution 5 having 33.3 wt % of 1,4-diazabicyclo[2.2.2]octane-2-methanol (exemplified compound No. 2-1) dissolved in dipropylene glycol and catalyst solution 1 having 33.3 wt % of 3-hydroxy-1,5-diazabicyclo[3.2.2]nonane (exemplified compound No. 1-1) dissolved in dipropylene glycol, were mixed in the blend ratios as shown in Table 7 to prepare catalyst compositions C-1 to C-7 of the present invention. Further, the amine composition obtained in Preparation Example 3 was also used as catalyst composition C-8 for evaluation.

TABLE 7

| Catalyst composition No. | Blend ratio of catalysts |
|---|---|
| C-1 | Catalyst solution 5 [a]/Catalyst solution 1 [b] = 95/5 |
| C-2 | Catalyst solution 5/Catalyst solution 1 = 90/10 |
| C-3 | Catalyst solution 5/Catalyst solution 1 = 80/20 |
| C-4 | Catalyst solution 5/Catalyst solution 1 = 70/30 |
| C-5 | Catalyst solution 5/Catalyst solution 1 = 100/0 |
| C-6 | Catalyst solution 5/Catalyst solution 1 = 65/35 |
| C-7 | Catalyst solution 5/Catalyst solution 1 = 0/100 |
| C-8 | Catalyst solution 5/Catalyst solution 1 = 7/1 |

[a] Catalyst solution 5: DPG solution of exemplified compound No. 2-1 (33 wt %)
[b] Catalyst solution 1: DPG solution of exemplified compound No. 1-1 (33 wt %)

The polyol, water, the cross-linker and the surfactant were mixed in the raw material blend ratio as shown in Table 8 to prepare premix A. 83.9 g of premix A was put into each of six 300 ml polyethylene cups. Further, catalysts of catalyst compositions C-1 to C-8 were, respectively, added in such an amount that the reactivity would be 35±1 seconds by the following gel time, and the temperature of each solution was adjusted to 20(C. Then, a polyisocyanate liquid (Coronate 1106, manufactured by Nippon Polyurethane Industry Co., Ltd.) having the temperature adjusted to 20(C in a separate container, was put into each of the cups of premix A in such an amount that the isocyanate index ([isocyanate group]/[OH group] (molar ratio)×100) would be 100 and quickly stirred at 6,000 rpm for 5 seconds by a stirrer. Thereafter, each mixed liquid thus mixed and stirred, was transferred to a 2 L polyethylene cup having the temperature adjusted to 60(C, and the reactivity during foaming was measured. Then, by increasing the amounts of the raw materials, in a similar operation, into a mold (made of aluminum and having internal dimensions of 35 cm×35 cm×10 cm) having the temperature adjusted to 60(C, the mixed liquid was introduced so that the full over-all density of the foam would be 51 kg/m3, and, after putting a lid, foamed and molded. After 5 minutes from the time when the mixed liquid was introduced, the foam was removed from the mold. With respect to the molded foam, the full over-all density of the foam, the amine catalyst volatilization amount and the foam odor were measured and compared. The results are shown in Table 9.

TABLE 8

| | Parts by weight (pbw) |
|---|---|
| Polyol A [1] | 98 |
| Polyol B [2] | 2 |
| Diethanolamine [3] | 0.65 |
| Water | 3.2 |
| Surfactant A [4] | 1 |
| Polymeric MDI [5] | Isocyanate INDEX 100 [6] |

[1] FA-703, polyether polyol manufactured by Sanyo Chemical Industries, Ltd. (OH value = 34 mgKOH/g)
[2] CP1421, polyol manufactured by Dow Chemical (OH value = 35 mgKOH/g)
[3] Cross-linker manufactured by Wako Pure Chemical Industries, Ltd.
[4] B4113, silicone-type surfactant manufactured by Goldschmidt
[5] Coronate 1106 manufactured by Nippon Polyurethane Industry Co., Ltd. (NCO amount: 31.8%)
[6] INDEX = (molar amount of NCO groups/molar amount of OH groups) × 100

TABLE 9

| | | Ex. 6 | Ex. 7 | Ex. 8 | Ex. 9 | Ex. 10 | Comp. Ex. 4 | Ex. 11 | Ex. 12 |
|---|---|---|---|---|---|---|---|---|---|
| Amount of catalyst (pbw) | | | | | | | | | |
| C-1 | | 3.71 | | | | | | | |
| C-2 | | | 3.69 | | | | | | |
| C-3 | | | | 3.67 | | | | | |
| C-4 | | | | | 3.63 | | | | |
| C-5 | | | | | | | 3.73 | | |
| C-6 | | | | | | | | 3.62 | |
| C-7 | | | | | | | | | 3.43 |
| C-8 | | | | | | 3.69 | | | |
| Catalyst activities | | ○ | ○ | ○ | ○ | ○ | — | ○ | ◎ |
| Reactivity (sec) | | | | | | | | | |
| Cream time | | 8 | 8 | 9 | 10 | 9 | 8 | 10 | 11 |
| Gel time | | 36 | 35 | 34 | 35 | 34 | 35 | 34 | 35 |
| Rise time | | 55 | 54 | 53 | 53 | 53 | 54 | 52 | 51 |
| Physical properties of foam | | | | | | | | | |
| Over-all density | (kg/m$^3$) | 50.8 | 50.1 | 51.1 | 50.7 | 50.6 | 51.8 | 51.8 | 51.4 |
| Amine catalyst volatilization amount (VOC) | (ppm) | <5 | <5 | <5 | <5 | <5 | 7 | 6 | 9 |
| Amine catalyst volatilization amount (Fogging) | (pm) | 39 | 37 | 40 | 41 | 35 | 43 | 44 | 56 |
| Foam odor | | ◎ | ◎ | ◎ | ○ | ◎ | Δ | Δ | X |

Here, the measurement items for reactivity (cream time, gel time, rise time and catalytic activity) and the measuring methods for the amine catalyst volatilization amount, etc. are the same as described above, and the measured values of VOC and Fogging are represented by the volatilization amount (ppm) of the amine catalyst per 1 g of the foam.

Further, the foam odor was evaluated as follows.

(Foam Odor)

A foam having a size of 5 cm×5 cm×3 cm was cut out from an upper portion of the free foaming process foam, of which the reactivity was measured, and put into a 900 ml standard glass bottle, which was then covered with a lid. This bottle was heated at 80° C. for 1 hour and then returned to room temperature, whereupon the foam odor was sniffed by ten monitors, and the intensity of the odor was determined by the following standards.

◎: Substantially no odor, ○: Sight odor, Δ: Distinct odor, x: Intensive odor

It is evident from the results in Examples 6 to 10 that as compared with a case where as in Comparative Example 4, a 1,4-diazabicyclo[2.2.2]octane-2-methanol is used alone, by the catalyst compositions of the present invention, the catalytic activities are improved, whereby it is possible to reduce the amounts to be used. As a result, the amount of a volatile organic compound (VOC) from the urethane foam derived from an amine catalyst was lower than the detectable lower limit of 5 ppm, and the urethane foam had substantially no odor.

Further, as shown in Examples 11 and 12, in a case where amine compound (A) represented by the above formula (1) like exemplified compound No. 1-1, is used alone or used in an amount exceeding a certain level, although the catalytic activity may be substantially improved, the VOC amount tends to increase. Accordingly, in order to further reduce the VOC amount, it is effective to use it in combination with amine compound (B) represented by the above formula (2) like exemplified compound No. 2-1.

Examples 13 to 15 and Comparative Example 5

Catalyst compositions C-9 to C-12 were prepared in the same compositions as in Examples 7 to 9 except that in Examples 7 to 9, instead of 1,4-diazabicyclo[2.2.2]octane-2-methanol (exemplified compound No. 2-1) as a component used for the preparation of catalyst compositions C-2 to C-5, 1,4-diazabicyclo[2.2.2]octane-2-ethanol represented by exemplified compound No. 2-8 obtained in Preparation Example 4 was used, and flexible high resilience polyurethane foams were produced. The results are shown in Table 10.

Here, with respect to the measurement items for reactivity (cream time, gel time, rise time and catalytic activity), the amine catalyst volatilization amount, the foam odor, etc., the measurements and evaluation were conducted in the same manner as described above.

TABLE 10

| | | Ex. 13 | Ex. 14 | Ex. 15 | Comp Ex. 5 |
|---|---|---|---|---|---|
| Amount of catalyst (pbw) [1] | | | | | |
| C-9 [2] | | 3.92 | | | |
| C-10 [3] | | | 3.86 | | |
| C-11 [4] | | | | 3.74 | |
| C-12 [5] | | | | | 4.06 |
| Catalyst activities | | ○ | ○ | ○ | Δ |
| Reactivity (sec) | | | | | |
| Cream time | | 8 | 8 | 9 | 7 |
| Gel time | | 35 | 35 | 35 | 35 |
| Rise time | | 55 | 54 | 53 | 56 |
| Physical properties of foam | | | | | |
| Over-all density | (kg/m$^3$) | 50.6 | 50.3 | 51.1 | 51.6 |
| Amine catalyst volatilization amount (VOC) | (ppm) | <5 | <5 | <5 | 6 |
| Amine catalyst volatilization amount (Fogging) | (pm) | 36 | 35 | 38 | 44 |
| Foam odor | | ◎ | ◎ | ◎ | Δ |

[1] As the catalyst, exemplified compound was used as diluted (33 wt %) with DPG (Amount includes DPG)
[2] Exemplified compound No. 2-8/exemplified compound No. 1-1 = 90/10
[3] Exemplified compound No. 2-8/exemplified compound No. 1-1 = 80/20
[4] Exemplified compound No. 2-8/exemplified compound No. 1-1 = 70/30
[5] Exemplified compound No. 2-8/exemplified compound No. 1-1 = 100/0

In Examples 13 to 15, like in Examples 6 to 10, the catalytic activities are improved, and it is possible to reduce the amounts to be used, as compared with the single system like in Comparative Example 5. As compared with exemplified compound No. 2-1, exemplified compound 2-8 showed a tendency that the amount of a volatile organic compound (VOC) from the urethane foam derived from the amine catalyst becomes small, although the amount of the catalyst to be used becomes large as the molecular weight is large.

Examples 16 and 17

Flexible high resilience polyurethane foams were prepared in the same manner as in Example 10 except that in Example 10, instead of the amine composition obtained in Preparation Example 3, the amine compositions obtained in Preparation Examples 5 and 6 were used. The respective amine compositions were diluted with DPG (to 33.3 wt %) to form catalyst compositions C-13 and C-14, respectively. The results are shown in Table 11.

Further, with respect to the measurement items for reactivity (cream time, gel time, rise time and catalytic activity), the amine catalyst volatilization amount, the foam odor, etc., the measurements and evaluation were conducted in the same manner as described above.

TABLE 11

|  |  | Ex. 16 | Ex. 17 |
|---|---|---|---|
| Amount of catalyst (pbw) [1] |  |  |  |
| C-13 [2] |  | 3.74 |  |
| C-14 [3] |  |  | 4.45 |
| Catalyst activities |  | ◯ | Δ |
| Reactivity (sec) |  |  |  |
| Cream time |  | 7 | 7 |
| Gel time |  | 35 | 35 |
| Rise time |  | 54 | 55 |
| Physical properties of foam |  |  |  |
| Over-all density | (kg/m$^3$) | 50.4 | 51.6 |
| Amine catalyst volatilization amount (VOC) | (ppm) | <5 | <5 |
| Amine catalyst volatilization amount (Fogging) | (pm) | 35 | <5 |
| Foam odor |  | ◎ | ◎ |

[1] As the catalyst, exemplified compound was used as diluted (33 wt %) with DPG (Amount includes DPG)
[2] Exemplified compound No. 2-2/exemplified compound No. 1-2 = 8/1
[3] Exemplified compound No. 2-6/exemplified compound No. 1-6 = 10/1

Catalyst composition C-14 used in Example 17 had two hydroxy groups reactive with isocyanate, whereby the amount of the catalyst to be added was required to be large as compared with other catalysts, but the amount of a volatile organic compound (VOC) from the obtainable foam was almost not detectable.

Preparation Example 7 (Synthesis of mixture of 3-dimethylaminopropylurea/N,N'-bis(3-dimethylaminopropyl)urea)

Into a 2 L separable flask, 360.4 g (6.0 mol) of urea and 429.3 g (4.2 mol) of N,N'-dimethylaminopropylamine were charged and heated at 120° C. for 4 hours. Then, after confirming that ammonia gas was no longer generated, the reaction was terminated, whereupon the obtained reaction liquid was cooled, and a volatile substance was removed by means of a vacuum pump. As a result of the measurement by HPLC (high performance liquid chromatography) analysis (Column: TSKgel SP-2SW, manufactured by Tosoh Corporation, eluent: acetonitrile/150 mM phosphate buffer=1/9, detector: UV-8020), the obtained product was a mixture of 3-dimethylaminopropylurea and N,N'-bis(3-dimethylaminopropyl)urea, whereby 3-dimethylaminopropylurea was obtained in an amount of 843.5 g (5.8 mol), and N,N'-bis(3-dimethylaminopropyl)urea was obtained in an amount of 191.7 g (0.8 mol).

Preparation Example 8 (Synthesis of mixture of 3-dimethylaminopropylurea/N,N'-bis(3-dimethylaminopropyl)urea)

Into a 2 L separable flask, 120.1 g (2.0 mol) of urea and 428.4 g (4.2 mol) of N,N-dimethylaminopropylamine were charged and heated at 120° C. for 4 hours. Then, after confirming that ammonia gas was no longer generated, the reaction was terminated, whereupon the obtained reaction liquid was cooled, and a volatile substance was removed by means of a vacuum pump. As a result of the measurement by HPLC analysis (Column: TSKgel SP-2SW, manufactured by Tosoh Corporation, eluent: acetonitrile/150 mM phosphate buffer=1/9, detector: UV-8020), the obtained product was a mixture of 3-dimethylaminopropylurea and N,N'-bis(3-dimethylaminopropyl)urea, whereby 3-dimethylaminopropylurea was obtained in an amount of 4.3 g (0.03 mol), and N,N'-bis(3-dimethylaminopropyl)urea was obtained in an amount of 452.9 g (1.97 mol).

Preparation Example 9 (Preparation of Aminourea Derivative Catalyst)

81 g of the mixture of 3-dimethylaminopropylurea/N,N'-bis(3-dimethylaminopropyl)urea obtained in Preparation Example 8 and 10 g of the mixture of 3-dimethylaminopropylurea/N,N'-bis(3-dimethylaminopropyl)urea obtained in Preparation Example 9 were mixed to prepare an aminourea derivative catalyst. As a result of the measurement by HPLC analysis (Column: TSKgel SP-2SW, manufactured by Tosoh Corporation, eluent: acetonitrile/150 mM phosphate buffer=1/9, detector: UV-8020), the obtained aminourea derivative catalyst contained 80.8 mol % of 3-dimethylaminopropylurea and 19.2 mol % of N,N'-bis(3-dimethylaminopropyl)urea.

Reference Example 5

The polyol, cell opener, cross-linker, surfactant and water were mixed in the raw material blend ratio as shown in Table 12 to prepare premix A. 148.1 g of premix A was put into a 500 ml polyethylene cup, and as catalysts, 1,4-diazabicyclo[2.2.2]octane-2-methanol (amine compound obtained in Preparation Example 1) and the aminourea derivative catalyst (catalyst prepared in Preparation Example 9) were added in the blend ratio as shown in Table 13, and the temperature of the solution was adjusted to 20° C.

TABLE 12

|  | Parts by weight (pbw) |
|---|---|
| Premix A |  |
| Polyol A [1] | 92.6 |
| Cell opener [2] | 1.9 |
| Diethanolamine [3] | 0.7 |

TABLE 12-continued

| | Parts by weight (pbw) |
|---|---|
| Silicone surfactant [4] | 1 |
| Water | 3.2 |

[1] FA-703, polyether polyol manufactured by Sanyo Chemical Industries, Ltd. (OH value = 34 mgKOH/g)
[2] Voranol-1421 manufactured by Dow Chemical
[3] Cross-linker manufactured by Aldrich
[4] Tegostab B4113LF manufactured by Eponic An isocyanate liquid having the temperature adjusted to 20° C. in a separate container, was put into the cup of premix A in such an amount that the isocyanate index [=isocyanate group/OH group (molar ratio)×100] would be 100 and quickly stirred at 6,000 rpm for 5 seconds by a stirrer. Thereafter, the mixed liquid thus mixed and stirred, was transferred to a 2 L (liter) polyethylene cup having the temperature adjusted to 60° C., and the reactivity during foaming was measured. Further, with respect to the obtained molded foam, the foam density was measured and compared. The results are shown in Table 13.

TABLE 13

| | Ref. Ex. 5 | Ex. 18 | Ex. 19 | Ex. 20 |
|---|---|---|---|---|
| Amount added (pbw) | | | | |
| Premix A | 148.1 | 148.1 | 148.1 | 148.1 |
| 1,4-Diazabicyclo[2.2.2]octane-2-methanol [1] | 0.75 | 0.66 | 0.57 | 0.47 |
| Aminourea derivative catalyst [2] | 0.25 | 0.25 | 0.25 | 0.25 |
| 1,5-Diazabicyclo[3.2.2]nonan-3-ol [3] | | 0.074 | 0.14 | 0.20 |
| Isocyanate [4] | | | | |
| Index [5] | 100 | 100 | 100 | 100 |
| Reactivity (sec) | | | | |
| Cream time | 16 | 15 | 15 | 16 |
| Gel time | 60 | 59 | 59 | 60 |
| Rise time | 83 | 83 | 82 | 83 |
| Physical properties of foam | | | | |
| Foam core density (kg/m³) | 37.8 | 38.1 | 38.4 | 38.3 |
| Foam odor | ◉ | ◉ | ◉ | ◉ |
| Foam moldability | ○ | ○ | ○ | ○ |

[1] Amine compound obtained in Preparation Example 1
[2] Catalyst prepared in Preparation Example 9
[3] Amine compound obtained in Preparation Example 2
[4] Coronate 1106 manufactured by Nippon Polyurethane Industry Co., Ltd.
[5] INDEX = (molar amount of NCO groups/molar amount of OH groups) × 100

Here, the methods for measurement of the respective measured items are as follows.

(1) Measured Items of the Reactivity

Cream time: The foaming initiation time and the time at the initiation of the rising of the foam were visually measured.

Gel time: As the reaction proceeded, the time when the liquid material turned into a resinous material was measured.

Rise time The time when the rising of the foam had terminated, was visually measured.

(2) Foam Core Density

A center portion of the molded foam was cut out in a size of 7 cm×7 cm×5 cm, and the size and the weight were accurately measured, whereupon the core density was calculated.

(3) Foam Odor

A foam having a size of 5 cm×5 cm×5 cm was cut out from the foam, of which the foam core density was measured, and put into a standard glass bottle, which was then covered with a lid. This bottle was heated at 80° C. for 1 hour and then, the bottle was cooled to room temperature, whereupon the foam odor was sniffed by ten monitors, and the intensity of the odor was measured and evaluated.

◉: Substantially no odor

○: Sight odor

Δ: Distinct odor x: Intensive odor (4) Foam Moldability

After 5 minutes of curing time, the foam was removed from the mold, and the appearance and stickiness were evaluated.

○: The appearance is good, and the foam is free from stickiness.

Δ: The appearance is good, but the foam has stickiness (the moldability is slightly poor).

x: Cells are roughened over the entire surface, and the appearance is defective (the moldability is poor).

Examples 18 to 20

Foams were prepared and evaluated in the same manner as in Reference Example 5 except that as the composition of catalyst compositions, 1,4-diazabicyclo[2.2.2]octane-2-methanol (amine compound obtained in Preparation Example 1), the aminourea derivative catalyst (catalyst prepared in Preparation Example 9) and 1,5-diazabicyclo[3.2.2]nonan-3-ol (amine compound obtained in Preparation Example 2) were used. The results are shown in Table 13 together with the results of Reference Example 5.

Comparative Examples 6 to 9

Foams were prepared and evaluated in the same manner as in Example 1 except that 1,4-diazabicyclo[2.2.2]octane-2-methanol (amine compound obtained in Preparation Example 1), the aminourea derivative catalyst (catalyst prepared in Preparation Example 9), a dipropylene glycol solution containing 33.3 wt % of triethylenediamine (tradename: TEDA-L33, manufactured by Tosoh Corporation) or a dipropylene glycol solution containing 70 wt % of bis(dimethylaminoethyl)ether (tradename: TOYOCAT-ET, manufactured by Tosoh Corporation) was used. The results are shown in Table 14.

TABLE 14

| | Comp. Ex. 6 | Comp. Ex. 7 | Comp. Ex. 8 | Comp. Ex. 9 |
|---|---|---|---|---|
| Amount added (pbw) | | | | |
| Premix A | 148.1 | 148.1 | 148.1 | 148.1 |
| 1,4-Diazabicyclo[2.2.2]octane-2-methanol [1] | | | 1.21 | |
| Aminourea derivative catalyst [2] | | | | 1.36 |
| TEDA-L33 [3] | 1.00 | 0.48 | | |
| TOYOCAT-ET [4] | | 0.12 | | |
| Isocyanate [5] | | | | |
| Index [6] | 100 | 100 | 100 | 100 |
| Reactivity (sec) | | | | |
| Cream time | 14 | 10 | 16 | 14 |
| Gel time | 59 | 60 | 60 | 59 |
| Rise time | 82 | 85 | 83 | 82 |

TABLE 14-continued

| | Comp. Ex. 6 | Comp. Ex. 7 | Comp. Ex. 8 | Comp. Ex. 9 |
|---|---|---|---|---|
| Physical properties of foam | | | | |
| Foam core density (kg/m³) | 37.3 | 38.8 | 37.3 | 39.7 |
| Foam odor | X | Δ | ⊚ | ○ |
| Foam moldability | Δ | ○ | Δ | X |

(1) Amine compound obtained in Preparation Example 1
(2) Catalyst prepared in Preparation Example 9
(3) Dipropylene glycol solution containing 33.3% of triethylenediamine (TEDA) manufactured by TOSOH CORPORATION TEDA-L33
(4) Dipropylene glycol solution containing 70% of bis(dimethylaminoethyl) ether manufactured by TOSOH CORPORATION TOYOCAT-ET
(5) Coronate 1106 manufactured by Nippon Polyurethane Industry Co., Ltd.
(6) INDEX = (molar amount of NCO groups/molar amount of OH groups) × 100

Examples 18 to 20 are examples in which the amine catalysts of the present invention were used. By further adding 1,5-diazabicyclo[3.2.2]nonane-3-ol to 1,4-diazabicyclo[2.2.2]octane-2-methanol and the aminourea derivative catalyst, it was possible to further improve the catalytic activities while maintaining the odor suppression of the amine catalyst from the foam and the foam moldability.

Further, it has been made evident that as compared with cases wherein a component of the amine catalyst, the aminourea derivative catalyst, etc., was used alone (Comparative Examples 8 and 9), the catalytic activities were improved, and they are catalysts excellent in the foam moldability.

On the other hand, in cases wherein a dipropylene glycol solution containing 33.3 wt % of triethylenediamine (tradename: TEDA-L33, manufactured by Tosoh Corporation) or a dipropylene glycol solution containing 70 wt % of bis (dimethylaminoethyl)ether (tradename: TOYOCAT-ET, manufactured by Tosoh Corporation), which is commonly used as a urethane catalyst, was used (Comparative Examples 6 and 7), although the foam moldability was excellent, an foam odor catalyst from the foam was confirmed, and it was not possible to prevent discoloration of PVC of automobile instrument panels, the Fogging phenomenon of window glass, etc. attributable to the amine catalyst.

INDUSTRIAL APPLICABILITY

The catalyst for producing a polyurethane resin of the present invention is capable of producing a polyurethane product having good formability with good productivity, and the polyurethane product thereby obtained does not cause the odor problem, or the toxicity or environmental problem and thus is highly useful for industrial applications.

The entire disclosures of Japanese Patent Application No. 2010-286693 filed on Dec. 22, 2010, Japanese Patent Application No. 2010-288889 filed on Dec. 24, 2010, Japanese Patent Application No. 2010-291795 filed on Dec. 28, 2010, Japanese Patent Application No. 2011-229142 filed on Oct. 18, 2011, Japanese Patent Application No. 2011-229143 filed on Oct. 18, 2011, Japanese Patent Application No. 2011-241495 filed on Nov. 2, 2011 and Japanese Patent Application No. 2011-256401 filed on Nov. 24, 2011 including specifications, claims, drawings and summaries are incorporated herein by reference in their entireties.

The invention claimed is:

1. A 3-hydroxy-1,5-diazabicyclo[3.2.2]nonane represented by the following formula (1), provided that when the compound represented by the formula (1) has optical isomers, diastereomers or geometric isomers, the compound includes both a mixture of any of them and an isolated isomer of any of them:

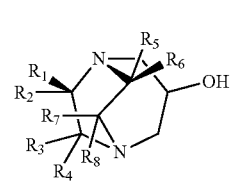

(1)

in the formula (1), each of $R_1$, $R_2$, $R_3$, $R_4$, $R_5$, $R_6$, $R_7$ and $R_8$ which are independent of one another, is a hydrogen atom, a $C_{1-4}$ alkyl group, a hydroxy group, a hydroxymethyl group or a $C_{1-4}$ alkoxy group.

2. The 3-hydroxy-1,5-diazabicyclo[3.2.2]nonane according to claim 1, wherein in the formula (1), at least one of $R_1$, $R_2$, $R_3$, $R_4$, $R_5$, $R_6$, $R_7$ or $R_8$ is a methyl group or a hydroxymethyl group.

3. The 3-hydroxy-1,5-diazabicyclo[3.2.2]nonane according to claim 1, wherein in the formula (1), $R_1$, $R_2$, $R_3$, $R_4$, $R_5$, $R_6$, $R_7$ and $R_8$ are all hydrogen atoms.

4. A catalyst for producing a polyurethane resin, which contains the 3-hydroxy-1,5-diazabicyclo[3.2.2]nonane as defined in claim 1.

5. A catalyst for producing a polyurethane resin, which contains a 3-hydroxy-1,5-diazabicyclo[3.2.2]nonane represented by the following formula (1), provided that when the compound represented by the formula (1) has optical isomers, diastereomers or geometric isomers, the compound includes both a mixture of any of them and an isolated isomer of any of them:

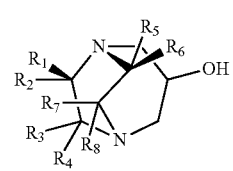

(1)

in the formula (1), each of $R_1$, $R_2$, $R_3$, $R_4$, $R_5$, $R_6$, $R_7$ and $R_8$ which are independent of one another, is a hydrogen atom, a $C_{1-4}$ alkyl group, a hydroxy group, a hydroxymethyl group or a $C_{1-4}$ alkoxy group, and a hydroxyalkyl-substituted-1,4-diazabicyclo[2.2.2]octane represented by the following formula (2), provided that when the compound represented by the formula (2) has optical isomers, diastereomers or geometric isomers, the compound includes both a mixture of any of them and an isolated isomer of any of them:

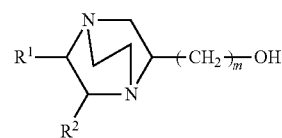

(2)

in the formula (2), each of $R^1$ and $R^2$ which are independent of each other, is a hydrogen atom, a $C_{1-4}$ alkyl group, a hydroxy group, a hydroxymethyl group or a $C_{1-4}$ alkoxy group, and m is 1 or 2.

6. The catalyst for producing a polyurethane resin according to claim 5, wherein in the formula (2), each of $R^1$ and $R^2$ is a hydrogen atom, a methyl group, an ethyl group or a hydroxymethyl group (provided that $R^1$ and $R^2$ are not all the same substituents).

7. The catalyst for producing a polyurethane resin according to claim 5, wherein in the formula (2), $R^1$ and $R^2$ are all hydrogen atoms.

8. The catalyst for producing a polyurethane resin according to claim 5, wherein a weight ratio of the 3-hydroxy-1,5-diazabicyclo[3.2.2]nonane to the hydroxyalkyl-substituted-1,4-diazabicyclo[2.2.2]octane is 0.01:1 to 0.3:1.

9. A catalyst for producing a polyurethane resin, which contains a 3-hydroxy-1,5-diazabicyclo[3.2.2]nonane represented by the following formula (1), provided that when the compound represented by the formula (1) has optical isomers, diastereomers or geometric isomers, the compound includes both a mixture of any of them and an isolated isomer of any of them:

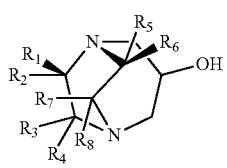

(1)

in the formula (1), each of $R_1$, $R_2$, $R_3$, $R_4$, $R_5$, $R_6$, $R_7$ and $R_8$ which are independent of one another, is a hydrogen atom, a $C_{1-4}$ alkyl group, a hydroxy group, a hydroxymethyl group or a $C_{1-4}$ alkoxy group;

a hydroxyalkyl-substituted-1,4-diazabicyclo[2.2.2]octane represented by the following formula (2), provided that when the compound represented by the formula (2) has optical isomers, diastereomers or geometric isomers, the compound includes both a mixture of any of them and an isolated isomer of any of them:

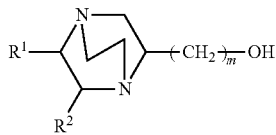

(2)

in the formula (2), each of $R^1$ and $R^2$ which are independent of each other, is a hydrogen atom, a $C_{1-4}$ alkyl group, a hydroxy group, a hydroxymethyl group or a $C_{1-4}$ alkoxy group, and m is 1 or 2; and
an aminourea derivative.

10. The catalyst for producing a polyurethane resin according to claim 9, wherein the hydroxyalkyl-substituted-1,4-diazabicyclo[2.2.2]octane is an amine compound represented by the following formula (2a):

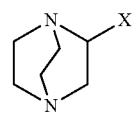

(2a)

in the formula (2a), X is a hydroxymethyl group or a hydroxyethyl group.

11. The catalyst for producing a polyurethane resin according to claim 9, wherein the aminourea derivative is at least one member selected from the group consisting of a mono(tertiary aminoalkyl)urea, a bis(tertiary aminoalkyl) urea and a mixture thereof.

12. The catalyst for producing a polyurethane resin according to claim 9, wherein the aminourea derivative is one or more compounds selected from the group consisting of 2-dimethylaminoethylurea, N,N'-bis(2-dimethylaminoethyl)urea, N,N-bis(2-dimethylaminoethyl)urea, 3-dimethylaminopropylurea, N,N'-bis(3-dimethylaminopropyl)urea, N,N-bis(3-dimethylaminopropyl)urea, 1-(N-methyl-3-pyrrolidino)methylurea, 1,3-bis(N-methyl-3-pyrrolidino) methylurea, 3-piperidinopropylurea, N,N'-bis(3-piperidinopropyl)urea, 3-morpholinopropylurea, N,N'-bis(3-morpholinopropyl)urea, 2-piperidinoethylurea, N,N'-bis(2-piperidinoethyl)urea, 2-morpholinoethylurea and N,N'-bis(2-morpholinoethyl)urea.

13. The catalyst for producing a polyurethane resin according to claim 4, which does not contain lead, tin, mercury or any compound thereof.

14. A process for producing a polyurethane resin, which comprises reacting a polyol and a polyisocyanate in the presence of the catalyst for producing a polyurethane resin as defined in claim 4.

15. The process for producing a polyurethane resin according to claim 14, wherein the amount of the catalyst for producing the polyurethane resin is within a range of from 0.01 to 30 parts by weight per 100 parts by weight of the polyol.

* * * * *